US009297025B2

(12) United States Patent
Christensen et al.

(10) Patent No.: US 9,297,025 B2
(45) Date of Patent: Mar. 29, 2016

(54) CONVERSION OF SOMATIC CELLS TO INDUCED REPROGRAMMED NEURAL STEM CELLS (IRNSCS)

(71) Applicant: Hoffmann-La Roche Inc., Nutley, NJ (US)

(72) Inventors: Klaus Christensen, Oberwil BL (CH); Martin Graf, Zeiningen (CH); Roberto Iacone, Basel (CH); Ravi Jagasia, Loerrach (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 104 days.

(21) Appl. No.: 13/769,762

(22) Filed: Feb. 18, 2013

(65) Prior Publication Data

US 2014/0051171 A1 Feb. 20, 2014

Related U.S. Application Data

(63) Continuation of application No. PCT/EP2011/064051, filed on Aug. 16, 2011.

(30) Foreign Application Priority Data

Aug. 19, 2010 (EP) .................................... 10173455

(51) Int. Cl.
*C12N 15/86* (2006.01)
*C12N 5/0797* (2010.01)

(52) U.S. Cl.
CPC .............. *C12N 15/86* (2013.01); *C12N 5/0623* (2013.01); *C12N 2501/11* (2013.01); *C12N 2501/115* (2013.01); *C12N 2501/119* (2013.01); *C12N 2501/13* (2013.01); *C12N 2501/405* (2013.01); *C12N 2501/60* (2013.01); *C12N 2501/602* (2013.01); *C12N 2501/727* (2013.01); *C12N 2506/1307* (2013.01); *C12N 2510/00* (2013.01)

(58) Field of Classification Search
CPC .. C12N 15/86; C12N 5/0623; C12N 2501/11; C12N 2501/115; C12N 2501/119; C12N 2501/13; C12N 2501/405; C12N 2501/60; C12N 2501/602; C12N 2501/727; C12N 2506/1307; C12N 2510/00
See application file for complete search history.

(56) References Cited

U.S. PATENT DOCUMENTS

| | | | |
|---|---|---|---|
| 2009/0047263 | A1 | 2/2009 | Yamanaka et al. |
| 2010/0021437 | A1 | 1/2010 | Isacson et al. |
| 2010/0144031 | A1 | 6/2010 | Jaenisch et al. |
| 2011/0076256 | A1 | 3/2011 | Park |

FOREIGN PATENT DOCUMENTS

| | | | |
|---|---|---|---|
| EP | 1516926 | A1 | 3/2005 |
| WO | 99/11758 | | 3/1999 |
| WO | 2005/095450 | A2 | 10/2005 |
| WO | 2010/018996 | A2 | 2/2010 |
| WO | 2010/089605 | A1 | 8/2010 |
| WO | 2012/022725 | A3 | 2/2012 |

OTHER PUBLICATIONS

Collas et al. Reproductive BioMedicine Online: 762-770, 2006.*
Oliveri et al. Regenerative Medicine, 2(5): 795-816, Sep. 2007.*
Sullivan et al. Reproductive BioMed. Online, 16(1): 41-50, Nov. 2008.*
Djuric and Ellis, 202, Stem Cell Research and Therapy, 2010,1:3.*
Cyranoski, Nature, 516: 162-164, 2014.*
Patel et al., Stem Cell Rev., 6(3): 367-380, 2010.*
Aasen et al., Nature Biotechnology, 26(11): 1276-1284, 2008.*
Zou et al., Journal of Biological Chemistry, 289(2): 5250-5260, 2014.*
Ring et al., Cell Stem Cell, 11(1): 100-109, 2012.*
Stadtfeld. Science, 322: 945-949, 2008.*
Okita. Science, 322: 949-953, 2008.*
Gonzalez PNAS, 106(22): 8918-8922, 2009.*
Maucksch et al., Stem Cells Translational Medicine, 2: 579-583, 2013.*
Moon et al., "Induction of neural stem cell-like cells (NSCLCs) from mouse astrocytes by Bmil" Biochemical and Biophysical Research Communications 371:267-272 ( 2008).
Onorati et al., "Neuropotent self-renewing neural stem (NS) cells derived from mouse induced pluripotent stem (iPS) cells" Molecular and Cellular Neuroscience 43:287-295 (2010).
Takahashi et al., "Induction of Pluripotent Stem Cells from Mouse Embryonic and Adult Fibroblast Cultures by Defined Factors" Cell 126:663-676 (Aug. 25, 2006).
Vierbuchen et al., "Direct conversion of fibroblasts to functional neurons by defined factors" Nature 463:1035-1042 (Feb. 25, 2010).
"PCT ISR and Written Opinion of the ISA for PCT/EP2011/064051", 2012.
Huangfu et al., "Induction of pluripotent stem cells from primary human fibroblasts with only Oct4 and Sox2" Nature Biotechnology 26(11):1269-1275 (Nov. 2008).
Masip et al., "Reprogramming with defined factors: from induced pluripotency to induced transdifferentiation" Molecular Human Reproduction 16(11):856-868 (Jul. 2010).
Kim et al., "Pluripotent stem cells induced from adult neural stem cells by reprogramming with two factors" Nature 454:646-651 (Jul. 2008).
Jing Ding et al., "Fasudil, a Rho kinase inhibitor, drives mobilization of adult neural stem cells after hypoxia/reoxygenation injury in mice" Molecular and Cellular Neuroscience 43(2):201-208 ( 2010).

* cited by examiner

*Primary Examiner* — Thaian N Ton
(74) *Attorney, Agent, or Firm* — Hoffmann-La Roche Inc.

(57) ABSTRACT

This application relates to a method for converting somatic cells to Neural Stem Cells (NSCs). Moreover this application relates to a method for converting human fibroblasts, keratinocytes or adipocytes to neural stem cells based on linked steps of genes transduction and chemically defined medium induction.

12 Claims, 10 Drawing Sheets

A) Phase 2.5X Obj.

Phase 10X Obj.

SEQUENCE LISTING

```
<160> NUMBER OF SEQ ID NOS: 10

<210> SEQ ID NO 1
<211> LENGTH: 954
<212> TYPE: DNA
```

<213> ORGANISM: Homo sapiens

<400> SEQUENCE: 1

```
atgtacaaca tgatggagac ggagctgaag ccgccgggcc cgcagcaaac ttcggggggc     60
ggcggcggca actccaccgc ggcggcggcc ggcggcaacc agaaaaacag cccggaccgc    120
gtcaagcggc ccatgaatgc cttcatggtg tggtcccgcg ggcagcggcg caagatggcc    180
caggagaacc ccaagatgca caactcggag atcagcaagc gcctgggcgc cgagtggaaa    240
cttttgtcgg agacggagaa gcggccgttc atcgacgagg ctaagcggct gcgagcgctg    300
cacatgaagg agcacccgga ttataaatac cggccccggc ggaaaaccaa gacgctcatg    360
aagaaggata agtacacgct gcccggcggg ctgctggccc ccggcggcaa tagcatggcg    420
agcggggtcg gggtgggcgc cggcctgggc gcgggcgtga accagcgcat ggacagttac    480
gcgcacatga acggctggag caacggcagc tacagcatga tgcaggacca gctgggctac    540
ccgcagcacc cgggcctcaa tgcgcacggc gcagcgcaga tgcagcccat gcaccgctac    600
gacgtgagcg ccctgcagta caactccatg accagctcgc agacctacat gaacggctcg    660
cccacctaca gcatgtccta ctcgcagcag ggcacccctg gcatggctct tggctccatg    720
ggttcggtgg tcaagtccga ggccagctcc agcccccctg tggttacctc ttcctcccac    780
tccagggcgc cctgccaggc cggggacctc cgggacatga tcagcatgta tctccccggc    840
gccgaggtgc cggaacccgc cgcccccagc agacttcaca tgtcccagca ctaccagagc    900
ggcccggtgc ccggcacggc cattaacggc acactgcccc tctcacacat gtga          954
```

<210> SEQ ID NO 2
<211> LENGTH: 1332
<212> TYPE: DNA
<213> ORGANISM: Homo sapiens

<400> SEQUENCE: 2

```
atggcgaccg cagcgtctaa ccactacagc ctgctcacct ccagcgcctc catcgtgcac     60
gccgagccgc ccggcggcat gcagcagggc gcgggggggct accgcgaagc gcagagcctg    120
gtgcagggcg actacggcgc tctgcagagc aacggacacc cgctcagcca cgctcaccag    180
tggatcaccg cgctgtccca cggcggcggc ggcgggggcg gtggcggcgg cgggggggggc    240
gggggcggcg gcgggggcgg cggcgacggc tccccgtggt ccaccagccc cctgggccag    300
ccggacatca agccctcggt ggtggtgcag cagggcggcc gcggagacga gctgcacggg    360
ccaggcgccc tgcagcagca gcatcagcag cagcaacagc aacagcagca gcaacagcag    420
caacagcagc agcagcagca gcaacagcgg ccgccgcatc tggtgcacca cgccgctaac    480
caccacccgg gacccggggc atggcggagc gcggcggctg cagcgcacct cccaccctcc    540
atgggagcgt ccaacggcgg cttgctctac tcgcagccca gcttcacggt gaacggcatg    600
ctgggcgccg gcgggcagcc ggccggtctg caccaccacg gcctgcggga cgcgcacgac    660
gagccacacc atgccgacca ccacccgcac ccgcactcgc acccacacca gcagccgccg    720
cccccgccgc ccccgcaggg tccgcctggc cacccaggcg cgcaccacga cccgcactcg    780
gacgaggaca cgccgacctc ggacgacctg gagcagttcg ccaagcagtt caagcagcgg    840
cggatcaaac tgggatttac ccaagcggac gtggggctgg ctctgggcac cctgtatggc    900
aacgtgttct cgcagaccac catctgcagg tttgaggccc tgcagctgag cttcaagaac    960
atgtgcaagc tgaagccttt gttgaacaag tggttggagg aggcggactc gtcctcgggc   1020
agccccacga gcatagacaa gatcgcagcg caagggcgca agcggaaaaa gcggacctcc   1080
```

```
atcgaggtga gcgtcaaggg ggctctggag agccatttcc tcaaatgccc caagccctcg   1140

gcccaggaga tcacctccct cgcggacagc ttacagctgg agaaggaggt ggtgagagtt   1200

tggttttgta acaggagaca gaaagagaaa aggatgaccc ctcccggagg gactctgccg   1260

ggcgccgagg atgtgtacgg ggggagtagg gacactccac cacaccacgg ggtgcagacg   1320

cccgtccagt ga                                                       1332


<210> SEQ ID NO 3
<211> LENGTH: 981
<212> TYPE: DNA
<213> ORGANISM: Homo sapiens

<400> SEQUENCE: 3

atgcatcgaa caacgagaat caagatcact gagctaaatc cccacctgat gtgtgtgctt     60

tgtggagggt acttcattga tgccacaacc ataatagaat gtctacattc cttctgtaaa    120

acgtgtattg ttcgttacct ggagaccagc aagtattgtc ctatttgtga tgtccaagtt    180

cacaagacca gaccactact gaatataagg tcagataaaa ctctccaaga tattgtatac    240

aaattagttc cagggctttt caaaaatgaa atgaagagaa gaagggattt ttatgcagct    300

catccttctg ctgatgctgc caatggctct aatgaagata gaggagaggt tgcagatgaa    360

gataagagaa ttataactga tgatgagata ataagcttat ccattgaatt ctttgaccag    420

aacagattgg atcggaaagt aaacaaagac aaagagaaat ctaaggagga ggtgaatgat    480

aaaagatact tacgatgccc agcagcaatg actgtgatgc acttaagaaa gtttctcaga    540

agtaaaatgg acatacctaa tactttccag attgatgtca tgtatgagga ggaacccttta   600

aaggattatt atacactaat ggatattgcc tacatttata cctggagaag gaatggtcca    660

cttccattga aatacagagt tcgacctact tgtaaaagaa tgaagatcag tcaccagaga    720

gatggactga caaatgctgg agaactggaa agtgactctg ggagtgacaa ggccaacagc    780

ccagcaggag gtattccctc cacctcttct tgtttgccta gccccagtac tccagtgcag    840

tctcctcatc cacagtttcc tcacatttcc agtactatga atggaaccag caacagcccc    900

agcggtaacc accaatcttc ttttgccaat agacctcgaa aatcatcagt aaatgggtca    960

tcagcaactt cttctggttg a                                              981


<210> SEQ ID NO 4
<211> LENGTH: 711
<212> TYPE: DNA
<213> ORGANISM: Homo sapiens

<400> SEQUENCE: 4

atggaaagct ctgccaagat ggagagcggc ggcgccggcc agcagcccca gccgcagccc     60

cagcagccct tcctgccgcc cgcagcctgt ttctttgcca cggccgcagc cgcggcggcc    120

gcagccgccg cagcggcagc gcagagcgcg cagcagcagc agcagcagca gcagcagcag    180

cagcaggcgc cgcagctgag accggcggcc gacggccagc cctcaggggg cggtcacaag    240

tcagcgccca agcaagtcaa gcgacagcgc tcgtcttcgc ccgaactgat gcgctgcaaa    300

cgccggctca acttcagcgg ctttggctac agcctgccgc agcagcagcc ggccgccgtg    360

gcgcgccgca acgagcgcga gcgcaaccgc gtcaagttgg tcaacctggg ctttgccacc    420

cttcgggagc acgtccccaa cggcgcggcc aacaagaaga tgagtaaggt ggagacactg    480

cgctcggcgg tcgagtacat ccgcgcgctg cagcagctgc tggacgagca tgacgcggtg    540
```

```
agcgccgcct tccaggcagg cgtcctgtcg cccaccatct cccccaacta ctccaacgac    600

ttgaactcca tggccggctc gccggtctca tcctactcgt cggacgaggg ctcttacgac    660

ccgctcagcc ccgaggagca ggagcttctc gacttcacca actggttctg a             711
```

<210> SEQ ID NO 5
<211> LENGTH: 1325
<212> TYPE: DNA
<213> ORGANISM: Homo sapiens

<400> SEQUENCE: 5

```
atggtgcagc aggcggagag cttggaagcg gagagcaacc tgccccggga ggcgctggac     60

acggaggagg gcgaattcat ggcttgcagc ccggtggccc tggacgagag cgacccagac    120

tggtgcaaga cggcgtcggg ccacatcaag cggccgatga acgcgttcat ggtatggtcc    180

aagatcgaac gcaggaagat catggagcag tctccggaca tgcacaacgc cgagatctcc    240

aagaggctgg gcaagcgctg gaaaatgctg aaggacagcg agaagatccc gttcatccgg    300

gaggcggagc ggctgcggct caagcacatg gccgactacc ccgactacaa gtaccggccc    360

cggaaaaagc ccaaaatgga cccctcggcc aagcccagcg ccagccagag cccagagaag    420

agcgcggccg gcggcggcgg cgggagcgcg ggcggaggcg cgggcggtgc caagacctcc    480

aagggctcca gcaagaaatg cggcaagctc aaggcccccg cggccgcggg cgccaaggcg    540

ggcgcgggca aggcggccca gtccggggac tacgggggcg cgggcgacga ctacgtgctg    600

ggcagcctgc gcgtgagcgg ctcgggcggc ggcggcgcgg gcaagacggt caagtgcgtg    660

tttctggatg aggacgacga cgacgacgac gacgacgacg agctgcagct gcagatcaaa    720

caggagccgg acgaggagga cgaggaacca ccgcaccagc agctcctgca gccgccgggg    780

cagcagccgt cgcagctgct gagacgctac aacgtcgcca aagtgcccgc cagccctacg    840

ctgagcagct cggcggagtc ccccgaggga gcgagcctct acgacgaggt gcgggccggc    900

gcgacctcgg gcgccggggg cggcagccgc ctctactaca gcttcaagaa catcaccaag    960

cagcacccgc cgccgctcgc gcagcccgcg ctgtcgcccg cgtcctcgcg ctcggtgtcc   1020

acctcctcgt ccagcagcag cggcagcagc agcggcagca gcggcgagga cgccgacgac   1080

ctgatgttcg acctgagctt gaatttctct caaagcgcgc acagcgccag cgagcagcag   1140

ctgggggggcg gcgcggcggc cgggaacctg tccctgtcgc tggtggataa ggatttggat   1200

tcgttcagcg agggcagcct gggctcccac ttcgagttcc ccgactactg cacgccggag   1260

ctgagcgaga tgatcgcggg ggactggctg gaggcgaact tctccgacct ggtgttcaca   1320

tattg                                                               1325
```

<210> SEQ ID NO 6
<211> LENGTH: 2547
<212> TYPE: DNA
<213> ORGANISM: Homo sapiens

<400> SEQUENCE: 6

```
atgctgcaaa ctaaggatct catctggact ttgtttttcc tgggaactgc agtttctctg     60

caggtggata ttgttcccag ccagggggag atcagcgttg gagagtccaa attcttctta    120

tgccaagtgg caggagatgc caaagataaa gacatctcct ggttctcccc caatggagaa    180

aagctcaccc caaaccagca gcggatctca gtggtgtgga atgatgattc ctcctccacc    240

ctcaccatct ataacgccaa catcgacgac gccggcattt acaagtgtgt ggttacaggc    300

gaggatggca gtgagtcaga ggccaccgtc aacgtgaaga tctttcagaa gctcatgttc    360
```

```
aagaatgcgc caaccccaca ggagttccgg gagggggaag atgccgtgat tgtgtgtgat    420
gtggtcagct ccctcccacc aaccatcatc tggaaacaca aaggccgaga tgtcatcctg    480
aaaaaagatg tccgattcat agtcctgtcc aacaactacc tgcagatccg gggcatcaag    540
aaaacagatg agggcactta tcgctgtgag ggcagaatcc tggcacgggg ggagatcaac    600
ttcaaggaca ttcaggtcat tgtgaatgtg ccacctacca tccaggccag gcagaatatt    660
gtgaatgcca ccgccaacct cggccagtcc gtcaccctgg tgtgcgatgc cgaaggcttc    720
ccagagccca ccatgagctg gacaaaggat ggggaacaga tagagcaaga ggaagacgat    780
gagaagtaca tcttcagcga cgatagttcc cagctgacca tcaaaaaggt ggataagaac    840
gacgaggctg agtacatctg cattgctgag aacaaggctg gcgagcagga tgcgaccatc    900
cacctcaaag tctttgcaaa acccaaaatc acatatgtag agaaccagac tgccatggaa    960
ttagaggagc aggtcactct tacctgtgaa gcctccggag accccattcc ctccatcacc   1020
tggaggactt ctacccggaa catcagcagc gaagaaaaga ctctggatgg gcacatggtg   1080
gtgcgtagcc atgcccgtgt gtcgtcgctg accctgaaga gcatccagta cactgatgcc   1140
ggagagtaca tctgcaccgc cagcaacacc atcggccagg actcccagtc catgtacctt   1200
gaagtgcaat atgccccaaa gctacagggc cctgtggctg tgtacacttg ggaggggaac   1260
caggtgaaca tcacctgcga ggtatttgcc tatcccagtg ccacgatctc atggtttcgg   1320
gatggccagc tgctgccaag ctccaattac agcaatatca agatctacaa cacccccctct  1380
gccagctatc tggaggtgac cccagactct gagaatgatt ttgggaacta caactgtact   1440
gcagtgaacc gcattgggca ggagtccttg gaattcatcc ttgttcaagc agacaccccc   1500
tcttcaccat ccatcgacca ggtggagcca tactccagca cagcccaggt gcagtttgat   1560
gaaccagagg ccacaggtgg ggtgcccatc ctcaaataca aagctgagtg gagagcagtt   1620
ggtgaagaag tatggcattc caagtggtat gatgccaagg aagccagcat ggagggcatc   1680
gtcaccatcg tgggcctgaa gcccgaaaca acgtacgccg taaggctggc ggcgctcaat   1740
ggcaaagggc tgggtgagat cagcgcggcc tccgagttca agacgcagcc agtccaaggg   1800
gaacccagtg cacctaagct cgaagggcag atgggagagg atggaaactc tattaaagtg   1860
aacctgatca agcaggatga cggcggctcc cccatcagac actatctggt caggtaccga   1920
gcgctctcct ccgagtggaa accagagatc aggctcccgt ctggcagtga ccacgtcatg   1980
ctgaagtccc tggactggaa tgctgagtat gaggtctacg tggtggctga gaaccagcaa   2040
ggaaaatcca aggcggctca ttttgtgttc aggacctcgg cccagcccac agccatccca   2100
gccaacggca gccccacctc aggcctgagc accggggcca tcgtgggcat cctcatcgtc   2160
atcttcgtcc tgctcctggt ggttgtggac atcacctgct acttcctgaa caagtgtggc   2220
ctgttcatgt gcattgcggt caacctgtgt ggaaaagccg ggcccggggc caagggcaag   2280
gacatggagg agggcaaggc cgccttctcg aaagatgagt ccaaggagcc catcgtggag   2340
gttcgaacgg aggaggagag gaccccaaac catgatggag ggaaacacac agagcccaac   2400
gagaccacgc cactgacgga gcccgagaag ggccccgtag aagcaaagcc agagtgccag   2460
gagacagaaa cgaagccagc gccagccgaa gtcaagacgg tccccaatga cgccacacag   2520
acaaaggaga acgagagcaa agcatga                                       2547
```

<210> SEQ ID NO 7
<211> LENGTH: 1617
<212> TYPE: DNA

<213> ORGANISM: Homo sapiens

<400> SEQUENCE: 7

```
atgaccaccc caggaaaaga gaactttcgc ctgaaaagtt acaagaacaa atctctgaat     60
cccgatgaga tgcgcaggag gagggaggaa gaaggactgc agttacgaaa gcagaaaaga    120
gaagagcagt tattcaagcg gagaaatgtt gctacagcag aagaagaaac agaagaagaa    180
gttatgtcag atggaggctt tcatgaggct cagattagta acatggagat ggcaccaggt    240
ggtgtcatca cttctgacat gattgaaatg atattttcca aaagcccaga gcaacagctt    300
tcagcaacac agaaattcag gaagctgctt tcaaaagaac ctaaccctcc tattgatgaa    360
gttatcagca caccaggagt agtggccagg tttgtggagt tcctcaaacg aaaagagaat    420
tgtacactgc agtttgaatc agcttgggta ctgacaaata ttgcttcagg aaattctctt    480
cagacccgaa ttgtgattca ggcaggagct gtgcccatct tcatagagtt gctcagctca    540
gagtttgaag atgtccagga acaggcagtc tgggctcttg gcaacattgc tggagatagt    600
accatgtgca gggactatgt cttagactgc aatatccttc cccctctttt gcagttattt    660
tcaaagcaaa accgcctgac catgacccgg aatgcagtat gggctttgtc taatctctgt    720
agagggaaaa gtccacctcc agaatttgca aaggtttctc catgtctgaa tgtgctttcc    780
tggttgctgt ttgtcagtga cactgatgta ctggctgatg cctgctgggc cctctcatat    840
ctatcagatg gacccaatga taaaattcaa gcggtcatcg atgcgggagt atgtaggaga    900
cttgtggaac tgctgatgca taatgattat aaagtggttt ctcctgcttt gcgagctgtg    960
ggaaacattg tcacagggga tgatattcag acacaggtaa ttctgaattg ctcagctctg   1020
cagagtttat tgcatttgct gagtagccca aaggaatcta tcaaaaagga agcatgttgg   1080
acgatatcta atattacagc tggaaatagg gcacagatcc agactgtgat agatgccaac   1140
attttcccag ccctcattag tattttacaa actgctgaat ttcggacaag aaaagaagca   1200
gcttgggcca tcacaaatgc aacttctgga ggatcagctg aacagatcaa gtacctagta   1260
gaactgggtt gtatcaagcc gctctgtgat ctcctcacgg tcatggactc taagattgta   1320
caggttgccc taaatggctt ggaaaatatc ctgaggcttg gagaacagga agccaaaagg   1380
aatggcactg gcattaaccc ttactgtgct ttgattgaag aagcttatgg tctggataaa   1440
attgagttct tacagagtca tgaaaaccag gagatctacc aaaaggcctt tgatcttatt   1500
gagcattact tcgggaccga agatgaagac agcagcattg caccccaggt tgaccttaac   1560
cagcagcagt acatcttcca acagtgtgag gctcctatgg aaggtttcca gctttga      1617
```

<210> SEQ ID NO 8
<211> LENGTH: 1470
<212> TYPE: DNA
<213> ORGANISM: Homo sapiens

<400> SEQUENCE: 8

```
atgctggaca tgggagatag gaaagaggtg aaaatgatcc ccaagtcctc gttcagcatc     60
aacagcctgg tgcccgaggc ggtccagaac gacaaccacc acgcgagcca cggccaccac    120
aacagccacc acccccagca ccaccaccac caccaccacc atcaccacca cccgccgccg    180
cccgccccgc aaccgccgcc gccgccgcag cagcagcagc cgccgccgcc gccgcccccg    240
gcaccgcagc ccccccagac gcggggcgcc ccggccgccg acgacgacaa gggcccccag    300
cagctgctgc tcccgccgcc gccaccgcca ccaccggccg ccgccctgga cggggctaaa    360
gcggacgggc tgggcggcaa gggcgagccg ggcggcgggc cgggggagct ggcgcccgtc    420
```

```
gggccggacg agaaggagaa gggcgccggc gccggggggg aggagaagaa gggggcgggc    480

gagggcggca aggacgggga ggggggcaag gagggcgaga agaagaacgg caagtacgag    540

aagccgccgt tcagctacaa cgcgctcatc atgatggcca tccggcagag ccccgagaag    600

cggctcacgc tcaacggcat ctacgagttc atcatgaaga acttccctta ctaccgcgag    660

aacaagcagg gctggcagaa ctccatccgc cacaatctgt ccctcaacaa gtgcttcgtg    720

aaggtgccgc gccactacga cgacccgggc aagggcaact actggatgct ggacccgtcg    780

agcgacgacg tgttcatcgg cggcaccacg ggcaagctgc ggcgccgctc caccacctcg    840

cgggccaagc tggccttcaa gcgcggtgcg cgcctcacct ccaccggcct caccttcatg    900

gaccgcgccg gctccctcta ctggcccatg tcgcccttcc tgtccctgca ccaccccgc     960

gccagcagca ctttgagtta caacggcacc acgtcggcct accccagcca ccccatgccc   1020

tacagctccg tgttgactca gaactcgctg ggcaacaacc actccttctc caccgccaac   1080

ggcctgagcg tggaccggct ggtcaacggg gagatcccgt acgccacgca ccacctcacg   1140

gccgccgcgc tagccgcctc ggtgccctgc ggcctgtcgg tgccctgctc tgggacctac   1200

tccctcaacc cctgctccgt caacctgctc gcgggccaga ccagttactt tttcccccac   1260

gtcccgcacc cgtcaatgac ttcgcagagc agcacgtcca tgagcgccag ggccgcgtcc   1320

tcctccacgt cgccgcaggc cccctcgacc ctgccctgtg agtctttaag accctctttg   1380

ccaagtttta cgacgggact gtctggggga ctgtctgatt atttcacaca tcaaaatcag   1440

gggtcttctt ccaacccttt aatacattaa                                    1470


<210> SEQ ID NO 9
<211> LENGTH: 2908
<212> TYPE: DNA
<213> ORGANISM: Homo sapiens

<400> SEQUENCE: 9

cgggcgccgc aggagcgagt gagctgggag cgaggggcga aggcgcggag aagcccggcc     60

gcccggtggg cggcagaagg ctcagccgag gcggcggcgc cgactccgtt ccactctcgg    120

cccggatcca ggcctccggg ttcccaggcg ctcacctccc tctgacgcac tttaaagagt    180

ctcccccctt ccacctcagg gcgagtaata gcgaccaatc atcaagccat ttaccaggct    240

tcggaggaag ctgtttatgt gatccccgca ctaattaggc tcatgaacta acaaatcgtt    300

tgcacaactt gtgaagaagc gaacacttcc atggattgtc cttggactta gggcgccctg    360

cccgcctttt gcagaggaga aaaaactttt tttttttttt gcctcccccg agaactttcc    420

cccctcctcc tccctgcctc taactccgat ccccccacgc catctcgcca aaaaaaaaaa    480

aaaaaaaaaa aaagaaaaaa aaagaaaaaa aaagaaaaaa aattacccca atccacgcct    540

gcaaattctt ctggaaggat tttcccccct ctcttcaggt tgggcgcgtt tggtgcaaga    600

ttctcgggat cctcggcttt gcctctccct ctccctcccc cctcctttcc tttttccttt    660

cctttccttt ctttcttcct ttccttcccc ccaccccac cccacccca aacaaacgag      720

tccccaattc tcgtccgtcc tcgccgcggg cagcgggcgg cggaggcagc gtgcggcggt    780

cgccaggagc tgggagccca gggcgcccgc tcctcggcgc agcatgttcc agccggcgcc    840

caagcgctgc ttcaccatcg agtcgctggt ggccaaggac agtcccctgc ccgcctcgcg    900

ctccgaggac cccatccgtc ccgcggcact cagctacgct aactccagcc ccataaatcc    960

gttcctcaac ggcttccact cggccgccgc cgccgccgcc ggtaggggcg tctactccaa   1020
```

```
cccggacttg gtgttcgccg aggcggtctc gcacccgccc aaccccgccg tgccagtgca   1080

cccggtgccg ccgccgcacg ccctggccgc ccacccccta ccctcctcgc actcgccaca   1140

ccccctattc gcctcgcagc agcgggatcc gtccaccttc taccccctggc tcatccaccg   1200

ctaccgatat ctgggtcatc gcttccaagg gaacgacact agccccgaga gtttcctttt   1260

gcacaacgcg ctggcccgaa agcccaagcg gatccgaacc gccttctccc cgtcccagct   1320

tctaaggctg gaacacgcct ttgagaagaa tcactacgtg gtgggcgccg aaaggaagca   1380

gctggcacac agcctcagcc tcacggaaac tcaggtaaaa gtatggtttc agaaccgaag   1440

aacaaagttc aaaaggcaga agctggagga agaaggctca gattcgcaac aaaagaaaaa   1500

agggacgcac catattaacc ggtggagaat cgccaccaag caggcgagtc cggaggaaat   1560

agacgtgacc tcagatgatt aaaaacataa acctaacccc acagaaacgg acaacatgga   1620

gcaaaagaga cagggagagg tggagaagga aaaaacccta caaaacaaaa acaaaccgca   1680

tacacgttca ccgagaaagg gagagggaat cggagggagc agcggaatgc ggcgaagact   1740

ctggacagcg agggcacagg gtcccaaacc gaggccgcgc caagatggca gaggatggag   1800

gctccttcat caacaagcga ccctcgtcta aagaggcagc tgagtgagag acacagagag   1860

aaggagaaag agggagggag agagagaaag agagagaaag agagagagag agagagagag   1920

agaaagctga acgtgcactc tgacaagggg agctgtcaat caaacaccaa accggggaga   1980

caagatgatt ggcaggtatt ccgtttatca cagtccactt aaaaaatgat gatgatgata   2040

aaaaccacga cccaaccagg cacaggactt ttttgttttt tgcacttcgc tgtgtttccc   2100

ccccatcttt aaaaataatt agtaataaaa aacaaaaatt ccatatctag ccccatccca   2160

cacctgtttc aaatccttga aatgcatgta gcagttgttg ggcgaatggt gtttaaagac   2220

cgaaaatgaa ttgtaatttt cttttccttt taaagacagg ttctgtgtgc tttttatttt   2280

gatttttttt cccaagaaat gtgcagtctg taaacacttt ttgatacctt ctgatgtcaa   2340

agtgattgtg caagctaaat gaagtaggct cagcgatagt ggtcctctta cagagaaacg   2400

gggagcagga cgacgggggg gctgggggtg gcgggggagg gtgcccacaa aaagaatcag   2460

gacttgtact gggaaaaaaa cccctaaatt aattatattt cttggacatt ccctttccta   2520

acatcctgag gcttaaaacc ctgatgcaaa cttctccttt cagtggttgg agaaattggc   2580

cgagttcaac cattcactgc aatgcctatt ccaaacttta aatctatcta ttgcaaaacc   2640

tgaaggactg tagttagcgg ggatgatgtt aagtgtggcc aagcgcacgg cggcaagttt   2700

tcaagcactg agtttctatt ccaagatcat agacttacta aagagagtga caaatgcttc   2760

cttaatgtct tctataccag aatgtaaata tttttgtgtt ttgtgttaat ttgttagaat   2820

tctaacacac tatatacttc caagaagtat gtcaatgtca atattttgtc aataaagatt   2880

tatcaatatg ccctcaaaaa aaaaaaaa                                       2908
```

<210> SEQ ID NO 10
<211> LENGTH: 2191
<212> TYPE: DNA
<213> ORGANISM: Homo sapiens

<400> SEQUENCE: 10

```
gcgacgaaag agaggatgcc tcttaaaggc agaagacttt aactaggggc gggcgagcag     60

atgtgtgaga tcttctattc aaagagtgga catatagccc agttttcaga gccacgtatt    120

cgagccccgt gggatccgga ggctgccaac cagctccagc atgcagaaca gtcacagcgg    180

agtgaatcag cttggtggtg tctttgtcaa cgggcggcca ctgccggact ccacccggca    240
```

-continued

```
gaagatcgta gagctagctc acagcggggc ccggccgtgc gacatttccc gaattctgca    300
ggtgtccaac ggatgtgtga gtaaaattct gggcaggtat tacgagactg gctccatcag    360
acccagggca atcggaggca gtaagccaag agtggcgact ccagaagttg taagcaaaat    420
agcccagtat aaacgggagt gcccgtccat ctttgcttgg gaaatccgag acagattact    480
ctccgagggg gtctgtacca acgacaatat acccagtgtg tcatcaataa acagagttct    540
tcgcaacctg gctagcgaaa agcaacagat gggcgcagac ggcatgtatg ataaactaag    600
gatgctgaac ggacagaccg gaagctgggg cacccgccct ggttggtatc ccgggacgtc    660
agtaccaggg caacccacgc aagacggctg ccagcaacag gaaggacagg gagaaaacac    720
caactccatc agctccaatg gagaagactc ggatgaggct caaatgcggc tgcagctgaa    780
gcggaagctg cagagaaata gaacatcttt tacccaggag cagattgagg ctctggagaa    840
agagtttgag aggacccatt atccagatgt gtttgcccgg gaaagactag cagccaaaat    900
agatctacct gaagcaagga tacaggtgtg gttttctaac cgaagggcca agtggagaag    960
agaagaaaaa ctgaggaacc agagaagaca ggccagcaac accccgagtc acatccctat   1020
cagcagcagt ttcagtacca gtgtctacca gccaattcca cagcccacca cacctgtctc   1080
ctcctttaca tcgggttcca tgttgggccg cacagacacc gccctcacca acacgtacag   1140
tgctttgccg ccgatgccca gcttcaccat ggcaaataac ctgcctatgc aacccccagt   1200
ccccagtcag acctcctcgt actcctgcat gctgcccacc agcccttcag tgaatgggcg   1260
gagttatgat acctacaccc ctccgcacat gcaaacacac atgaacagtc agcccatggg   1320
cacctcggga accacttcaa caggactcat ttcacctgga gtgtcagttc ccgtccaagt   1380
tcccggaagt gaacctgaca tgtctcagta ctggcctcga ttacagtaaa gagagagaaa   1440
gagagagaat gtgatcgaga gggggattgt gttcactcag ccaatgacta tgtggacaca   1500
gcggttgggt attcaggaaa gaaagagaaa tggctgttag aagcacttca ctttacaact   1560
gtgtcctata ctggagcccg ggaatggact agaaaccagg acctttgcgt acagaaggca   1620
cggtatcagt tggaacaaat cttcattttg gtatccaaac ttttattcat tttggtgtat   1680
tatttgtaaa tgggcatttg tatgttataa tgaagaaaag aacaacacag gctgttggat   1740
cttggatctg tgttggctca tgtggttgtt taaaggaaac catgatcgac aagatttgcc   1800
atggatttaa gagttttatc aagatatatc gaatacttct acccatctgt tcatagttta   1860
tggactgatg ttccaagttt gtatcattcc tttgcatata attaaacatg gaacaacata   1920
cactagatat atgtaaaaaa tatctgttgg tttttccaaa ggttgttaac agataaagtt   1980
tatgtgcaaa aaagggtaag atatgaattc gaggagaagt tgatagctaa aaggtagagt   2040
gtgtcttcga tataatccaa tttgttttat gtcaaaatgt aagtatttgt cttccctaga   2100
aatcctcaga atgatttcta taataaagtt aatttcattt atatttgaaa aaaaaaaaaa   2160
aaaaaaaaaa aaaaaaaaaa aaaaaaaaaa a                                  2191
```

CONVERSION OF SOMATIC CELLS TO INDUCED REPROGRAMMED NEURAL STEM CELLS (IRNSCS)

CROSS REFERENCE TO RELATED APPLICATIONS

This application is a continuation of International Application No. PCT/EP2011/064051 having an international filing date of Aug. 16, 2011, the entire contents of which are incorporated herein by reference and which claims benefit under 35 U.S.C. §119 to European Patent Application No. 10173455.6 filed Aug. 19, 2010.

SEQUENCE LISTING

The instant application contains a Sequence Listing submitted via EFS-Web and is hereby incorporated by reference in its entirety. Said ASCII copy, created on Feb. 15, 2013, is named P5509C1_SeqList.txt, and is 22,275 bytes in size.

FIELD OF THE INVENTION

This application relates to a method for converting somatic cells to Neural Stem Cells (NSCs). Moreover this application relates to a method for converting human fibroblasts, kerotinocytes or adipocytes to neural stem cells based on linked steps of genes transduction and chemically defined medium induction.

BACKGROUND OF THE INVENTION

The dogma that fully differentiated somatic cells have absolutely irreversible properties was generally accepted for a long time. This began to change when a series of pioneering experiments showed that silent gene expression profiles can be completely reactivated by the fusion of different pairs of cell types (Blau, H. M. How fixed is the differentiated state? Lessons from heterokaryons. Trends Genet. 5, 268-272 (1989)). More recently it was shown that transfer of nuclei from a somatic cell type into an enucleated egg cell could lead to the complete reversion of the somatic cells' gene expression profile, and to the formation of a pluripotent cell state able to generate new entire animals (see e.g. Gurdon, J. B. & Melton, D. A. Nuclear reprogramming in cells. Science 322, 1811-1815 (2008)). Yamanaka and colleagues (Takahashi, K. & Yamanaka, S. Induction of pluripotent stem cells from mouse embryonic and adult fibroblast cultures by defined factors. Cell 126, 663-676 (2006)) demonstrated that somatic cells can be reprogrammed to induced pluripotent stem cells (iPSCs) by transduction of four defined factors (Sox2, Oct4, Klf4, c-Myc). Different types of somatic cells including fibroblasts, keratynocytes and adipocytes have been reprogrammed to an iPSC pluripotent state. During the past years the question arose whether specific somatic cell types could be transdifferentiated to a completely different somatic cell type such as a neuron. Wernig and colleagues addressed this question showing the direct conversion of mouse fibroblasts to functional neurons by transduction of three crucial genes: Mash1, Brn2 and Myt11 (Wernig at al. Direct conversion of fibroblasts to functional neurons by defined factors. Nature 25; 463(7284):1035-41 (2010). However the neurons obtained are postmitotic cells which are by definition not able to proliferate and which do not tolerate freezing and thawing procedures. US2010/0021437 discloses a method for generating induced pluripotent stem cells from fibroblasts and inducing those cells to differentiate into neural phenotypes.

However, direct conversion of differentiated somatic cells to neural stem cells has not been described so far. Neural stem cells are multipotent stem cells and are reported to be propagated under specific conditions. They require a chemically defined medium, for example N2B27 medium (N2B27 is a 1:1 mixture of DMEM/F12 (Gibco, Paisley, UK) supplemented with N2 and B27 (both from Gibco)) supplemented with FGF (fibroblast growth factor 2) and EGF (epidermal growth factor). They can grow as a monolayer adherent culture, e.g. on Poly-ornithine/Lamin coated plate or as floating neurospheres in non-adherent cell culture plates. The two types of neural stem cell cultures (neurospheres, adherent cultures) have been reported to be completely inter-convertible. Neural stem cells can be grown indefinitely and still remain truly multipotent. Upon special conditions they differentiate into the cell types that compose the adult brain, including neurons, astrocytes and oligodendrocytes. Neural stem cells are considered possible therapeutic agents for treating patients with neurodegenerative diseases such as Alzheimer's disease, Parkinson's disease, stroke, and spinal cord injury.

SUMMARY OF THE INVENTION

It is known that neural stem cells can be generated either in vitro from Embryonic Stem Cells (ESCs) (Chambers et al. Nature 27; 3 (2009)) or they can be isolated directly from brain samples (Reynolds B A, Rietze R L (2005) Nat Methods 2:333-336). However these methods known so far have many major drawbacks as they either raise a number of highly sensitive ethical considerations and/or they necessitate complicated and laborious technologies which suffer from serious troubles with reproducibility. So far no method has been described wherein neural stem cells can be directly derived from differentiated somatic cells. In principle, neural stem cells could be obtained from iPSCs that have been derived from differentiated cells. However, this would imply culturing of iPSCs. iPSCs have been reported to expand indefinitely but the culture conditions are complicated and require huge efforts. In addition the derivation of neural stem cells from pluripotent stem cells has been reported to fluctuate due to stochastic mechanisms. A common obstacle of iPSCs and ESCs is that even a small number of undifferentiated cells can result in the formation of teratomas (germ cell tumors comprising several cell types), which pose serious contaminations that may not be ignored. Somatic stem cells, such as neural stem cells do not form teratomas. Hence there remains a need for an easy accessible and reproducible technology for the generation of neural stem cells. The present invention provides a method for converting somatic cells directly to neural stem cells. The new method alleviates the necessity of obtaining iPS cells and hence removes the risk of teratoma formation. Such cells without the ability to form teratomas are useful and safe for regenerative medicine applications. Preferably said somatic cells are mammalian somatic cells, most preferably human somatic cells. Said human somatic cells can be obtained from a healthy individual or from a patient. Preferably said somatic cells are fibroblast cells, adipocytes or keratinocytes, most preferably fibroblast cells. Said fibroblast cells, adipocytes or keratinocytes can be easily and safely derived from a patient or healthy individual, for example by non-invasive methods such as skin biopsy or from plucked hair. The method of this invention allows to convert somatic cells such as fibroblasts cells, adipocytes or keratinocytes from healthy or diseased individuals directly to neural stem cells. These healthy individuals or patients specific neural stem cells can be expanded indefinitely. Culturing is easy and well characterized. It is possible to freeze and thaw healthy individuals and patients specific neural stem cells aliquots reproducibly. In particular, patient derived neural stem cells represent a disease relevant in vitro model to study the pathophysiology of CNS diseases. Conversion of patients' specific somatic cells directly to neural stem cells represents an easy accessible and reproducible technology to generate BioBanks of patient specific neural stem cells. Such BioBanks have great relevance for CNS related diseases, as a clear pathology has been described in at least one of the three cell types generated from the neural stem cells: neurons, oligodentrocytes and astrocytes. Hence the neural stem cells obtained with the method described herein are valuable disease models to screen effective and safe drugs.

A variety of neurodegenerative diseases are characterized by neuronal cell loss. The regenerative capacity of the adult brain is rather limited in response to brain injury and neurodegenerative disease. Further, pharmacological interventions often become increasingly less effective as the susceptible neuronal populations are progressively lost. The neural stem cells obtained with the method described herein can also be used in regenerative medicine to treat neurodegenerative diseases like Parkinson's disease, Alzheimer's disease, Huntington's disease, Amyotrophic lateral sclerosis (ALS/Lou Gehrig's Disease) or spinal cord injury. With the innovative method described herein it is now possible to provide sufficient amounts of neuronal precursor cells for use in cell transplantation therapies. The neural stem cells can either be obtained from somatic cells isolated from a healthy individual or from a patient. Patient specific neural stem cells obtained by the method described herein are an attractive new donor source for autologous cell transplantation therapies, thereby abrogating any immune rejection due to immunological incompatibility between patient and donor. This strategy would eliminate the requirement of immune suppressants in cell transplantation therapy. Moreover, the creation of Biobanks of neural stem cells derived from healthy individuals with various HLA homozygous alleles can be used as donor banks for treatment of individuals in need. Heterologous transplantation of neural stem cells with a compatible HLA type reduces the risk of undesirable immune responses which could lead to rejection of the transplanted cells.

To achieve the inventive breakthrough described here, it was necessary to bypass some of the existing limitations of reprogramming, as well as to combine genes transduction with the employment of a step of induction with a specific medium.

Provided herein is a method for converting somatic cells to Neural Stem Cells (NSC), said method comprising the steps of:

a) providing somatic cells b) reprogramming said somatic cells to neural stem cells by introducing at least two genes and c) inducing for the reprogramming with growth factors and a small molecule;

In a further embodiment, said method additionally comprises d) incubating the product of step b) and c) under conditions suitable for proliferation of the neural stem cells. Typically the product of step b) and c) can be easily identified in a cell culture as neurospheres. Preferably said conditions suitable for proliferation of the neural stem cells comprise harvesting of said neurospheres and expanding them in a chemically defined medium. Preferably, said medium is an expansion medium and the neurospheres are cultured in non-adherent culturing conditions. Non-limiting examples of expansion media are described further below.

DETAILED DESCRIPTION OF THE INVENTION

The term "somatic cell" as used herein refers to any cell forming the body of an organism that are not germ line cells (e. g. sperm and ova, the cells from which they are made (gametocytes)) and undifferentiated stem cells. Internal organs, skin, bones, blood and connective tissue are all made up of somatic cells. Preferred somatic cells used in the method described herein are fibroblast cells, adipocytes or keratinocytes and are preferably obtained from skin biopsy.

Preferably, the somatic cells used for conversion into neural stem cells are of mammalian origin, most preferably of human origin. Said human somatic cells can be obtained from a healthy individual or from a patient. Preferably said somatic cells are chosen from the group of fibroblast cells, adipocytes or keratinocytes. These donor cells can be easily obtained from any suitable source. Preferred herein are sources that allow isolation of donor cells without invasive procedures on the human body. Methods for isolating fibroblast cells are well known in the art. Fibroblast cells may be obtained from any suitable source, for example from various organ tissues or skin tissue. Preferred fibroblasts are lung fibroblasts, foreskin fibroblasts, and adult dermal fibroblasts. In a special embodiment of this invention, said human fibroblasts are obtained from a patient, for example by skin biopsy (e.g. Reprogramming of human somatic cells to pluripotency with defined factors. George Q. Daley et al. Nature 2008; A method for the isolation and serial propagation of keratinocytes, endothelial cells, and fibroblasts from a single punch biopsy of human skin, Normand et al. In Vitro Cellular & Developmental Biology—Animal, 1995). Adipocytes and keratinocytes can also be easily derived by skin biopsy or plucked hair (Isolation and cultivation of human keratinocytes from skin or plucked hair for the generation of induced pluripotent stem cells, Belmonte et al. Nature Protocols 2010) and are also preferred donor cells for the method of this invention.

One preferred aspect of the present invention is a method for generating patient specific neural stem cells. Another aspect of the present invention is a method for generating neural stem cells from somatic cells obtained from a healthy individual.

As used herein, "neural stem cells" refers to a subset of pluripotent cells which express some neural markers including, for example, nestin. The neural stem cells obtained by the method described herein are also referred to as "irNSCs": induced reprogrammed neural stem cells. Neural stem cells can be expanded indefinitely and may differentiate into neurons or glial cells (e.g. astrocytes and oligodendrocytes). The term "patient specific neural stem cell" refers to neural stem cells obtained from somatic cells of a patient and are also referred to as autologous neural stem cells. "Neural stem cells obtained from a healthy individual" as used herein refers to neural stem cells obtained from somatic cells of an individual that is not suspected to suffer from any disorder or disease.

As used herein, the term "reprogramming" refers to one or more steps needed to convert a somatic cell to a less-differentiated cell, for example for converting fibroblast cells, adipocytes or keratinocytes into neural stem cells. Reprogramming of a somatic cell to a neural stem cell is achieved by introducing at least two genes involved in the maintenance of neural stem cell properties. Genes suitable for reprogramming of somatic cells to neural stem cells include, but are not limited to Sox2 (Seq ID No. 1), Brn2 (Seq ID No. 2), Bmi1 (Seq ID No. 3), Mash1 (Seq ID No. 4), Sox11 (Seq ID No. 5), NCam (Seq ID No. 6), Kpna1 (Seq ID No.7), Foxg1 (Seq ID No. 8), Emx2 (Seq ID No.9) and Pax6 (Seq ID No. 10). In a preferred embodiment at least two genes are introduced, in another preferred embodiment three genes are introduced. A preferred combination of genes to be introduced into the somatic cells comprises Bmi1 and Sox2. In a further preferred embodiment this combination of at least two genes additionally comprises Mash1. In another embodiment this combination of at least two genes additionally comprises one gene selected from the group of Mash1, Emx2, Foxg1, Pax6 and Sox11. In a further embodiment the combination of at least two genes comprises Bmi1 and Sox2 and Mash1.

The term "introducing of genes", as used herein, refers to any method that leads to the stable expression of said gene in a somatic cell. Said genes are introduced into somatic cells by methods known in the art, either by delivery into the cell via reprogramming vectors or by activation of said genes via small molecules. Examples of reprogramming vectors are retroviruses, lentiviruses, adenoviruses, plasmids and transposons. Preferred herein is the use of a lentivirus for the delivery of said genes. Examples of small molecules suitable for robust activation of said genes are DNA methylation inhibitors, histone deacytelase inhibitors, ergolines (e.g. lysergic acid ethylamide), flavones (e.g. 7' hydroxyflavone), paullones (e.g. Kenpaullone) (Reprogramming of murine fibroblasts to induced pluripotent stem cells with chemical complementation of Klf4 *PNAS* 2009 106 (22) 8912-8917), L-type channel agonists (e.g. BIX01294), BayK8644 and 5' azacytidine (Induction of Pluripotent Stem Cells from Mouse Embryonic Fibroblasts by Oct4 and Klf4 with Small-Molecule Compounds Yan Shi et al. Cell Stem Cell—6 Nov. 2008 (Vol. 3, Issue 5, pp. 568-574)). For successful induction of the reprogramming the somatic cells are grown in a suitable medium supplemented with growth factors and a small molecule. As used herein, the term "growth factor" means a biologically active polypeptide which causes cell proliferation, and includes both growth factors and their analogues. These include, without limitation, epidermal growth factor, transforming growth factors, nerve growth factor, acidic and basic fibroblast growth factor and angiogenesis factor, platelet-derived growth factor, insulin and insulin-like growth factors including somatomedins, myxoma and vaccinia virus-derived growth factors. Preferred growth factors used herein are BDNF (brain-derived neutrotrophic factor), FGF2 (fibroblast growth factor 2) and EGF (epidermal growth factor). The growth factors may be used alone or in pairwise combination, or most preferably all three factors are used together. In addition the fibroblasts are cultured in the presence of at least one small molecule. The term "small molecule", or "small compound" as used herein, refers to organic or inorganic molecules either synthesized or found in nature, generally having a molecular weight less than 10,000 grams per mole, optionally less than 5,000 grams per mole, and optionally less than 2,000 grams per mole. In one preferred embodiment said small molecule comprises an inhibitor of the Rho-associated coiled-coil forming protein serine/threonine kinase (ROCK) family of protein kinases.

Non-limiting examples of ROCK inhibitors comprise Fasudil (1-(5-Isoquinolinesulfonyl)homopiperazine), Thiazovivin (N-Benzyl-2-(pyrimidin-4-ylamino)thiazole-4-carboxamide), Y27632 ((+)-(R)-trans-4-(1-aminoethyl)-N-(4-pyridyl) cyclo-hexanecarboxamide dihydrochloride) and Balanol-like-324 compound (N-{(3R,4R)-4-[4-(2-Fluoro-6-hydroxy-3-methoxy-benzoyl)-benzoylamino]-azepan-3-yl}-4-hydroxy-3,5- dimethyl-benzamide). In another embodiment said small molecule is selected from an inhibitor of one or more of the kinases AMPK (AMP-activated protein kinase, beta 1 non-catalytic subunit; official symbol: PRKAB1), CHK2 (CHK2 checkpoint homolog (*S. pombe*), official symbol: CHEK2), MSK1 (ribosomal protein S6 kinase, 90 kDa, polypeptide 5; official symbol: RPS6KA5), PKA (protein kinase, cAMP-dependent, catalytic, alpha; official symbol: PRKACA), PKGa (protein kinase, cGMP-dependent, type I; official symbol: PRKG1) and SGK1 (serum/glucocorticoid regulated kinase 1, official symbol: SGK1).

A "suitable medium for induction of reprogramming", also depicted as "induction medium", as used herein refers to any chemically defined medium useful for induction of reprogramming of the somatic cells. Preferred herein is a serum free medium supplemented with insulin, transferrin and progesterone. Preferred media used herein contain 10-50 μg/ml insulin, 10-100 μg/ml transferrin and 10-50 nM progesterone. Examples of serum-free media suitable for induction of reprogramming are N2B27 medium (N2B27 is a 1:1 mixture of DMEM/F12 (Gibco, Paisley, UK) supplemented with N2 and B27 (both from Gibco)), N3 medium (composed of DMEM/F12 (Gibco, Paisley, UK), 25 μg/ml insulin, 50 μg/ml transferrin, 30 nM sodium selenite, 20 nM progesterone (Sigma), 100 nM putrescine (Sigma)), or NeuroCult® NS-A Proliferation medium (Stemcell Technologies). Most preferred herein is a serum free medium as described above which is additionally supplemented with FGF2, EGF, BDNF and a ROCK inhibitor. Preferably, said ROCK inhibitor comprises Fasudil or Balanol-like-324 compound. In a preferred embodiment, the medium is supplemented with 10-50 ng/ml FGF2, 10-50 ng/ml EGF, 1-20 ng/ml BDNF and 1-50 μM Fasudil or 1-10 μM Balanol-like-324 compound. After introduction of at least two genes the somatic cells to be reprogrammed are preferably grown in said induction medium for at least 1 day, preferably for 1 to 7 days, most preferably for 2 to 3 days.

In one embodiment the somatic cells of step a) are pretreated with a Histone Deacetylase (HDAC) inhibitor. "Pretreating" or "pretreatment" as used herein means incubation of the somatic cells in a suitable medium supplemented with said HDAC inhibitor for 4 to 60 hours, preferably 48 hours. HDAC inhibitors useful herein are selected from the group comprising sodium butyrate (butanoic acid, sodium salt) Trichostatin A (TSA, 7-[4-(dimethylamino)phenyl]-N-hydroxy-4,6-dimethyl-7-oxohepta-2,4-dienamide) and Valproic Acid (2-propyl-pentanoic acid). In one embodiment the somatic cells of step a) are pretreated with Valproic Acid. In another embodiment the somatic cells of step a) are pretreated with Valproic Acid for 48 hours.

For propagating proliferation of the neural stem cells as neurospheres cultures, the induced neural stem cells are grown in an expansion medium comprising a serum free medium supplemented with insulin, transferrin and progesterone and growth factors as described above. Preferably said growth factors comprise FGF2, BDNF and EGF. In another embodiment said expansion medium additionally comprises one or more supplements selected from the group of Heparin, Ascorbic Acid, SHH (Recombinant Human Sonic Hedgehog), FGF8 (Recombinant Human FGF8a Isoform), DLL4 (Recombinant Human DLL4), Jagged1 (Recombinant Human Jagged 1 Fc Chimera), Fasudil and Balanol-like-324 compound.

In another embodiment of the invention, the neural stem cells obtained by the method described herein are in a next step stimulated for differentiation by omission of at least one of the growth factors of the reprogramming medium. Preferably said growth factors to be withdrawn comprise EGF and FGF.

In another preferred embodiment of the invention, a marker gene is employed to facilitate screening and quantification of successfully reprogrammed neural stem cells. For example, a gene encoding for a fluorescent marker protein is introduced into the target somatic cells by lentivirus transduction. Examples of fluorescent marker proteins are GFP, YFP, EGFP or DsRed. Preferably said marker gene is operably linked to a nestin promoter. Nestin is specifically expressed in neural stem cells, therefore the marker gene under the control of a nestin promoter allows rapid screening and identification of induced reprogrammed neural stem cells. Thereafter, those cells are screened to identify a cell exhibiting the desired phenotype, i.e. neurospheres. Neurospheres bigger than 20 μm, preferably bigger than 50 μm, are selected and harvested for further expansion.

In another aspect of the invention, a population of neural stem cells produced by any of the foregoing methods is provided. Preferably, the population of neural stem cells is patient specific, i.e. derived from somatic cells obtained from diseased individuals. In another embodiment said population of stem cells is obtained from a healthy individual. The neural stem cells can be expanded indefinitely. Culturing is easy and well characterized. It is possible to freeze and thaw neural stem cells aliquots reproducibly. Patient derived neural stem cells represent a disease relevant in vitro model to study the pathophysiology of CNS diseases. Conversion of patients specific somatic cells directly to neural stem cells represents an easy accessible and reproducible technology to generate BioBanks of patient specific neural stem cells. Hence in a further preferred aspect of the invention a BioBank comprising patient specific neural stem cells is envisaged. In another embodiment, a BioBank comprising different populations of neural stem cells obtained from healthy individuals is generated. The term "BioBank" as used herein means a library of biological samples taken from different individuals or species. The archived collection of specimen and associated data is intended for research purposes with the aim of addressing neural diseases like neurodegenerative diseases such as Alzheimer's disease, Parkinson's disease, Huntington's disease, Amyotrophic lateral sclerosis (ALS/Lou Gehrig's Disease) stroke, and spinal cord injury or for therapy of said neurological diseases.

Another aspect of the invention is the use of neural stem cells obtained by this method. In a preferred embodiment the neural stem cells obtained by this method are used as in vitro model to study the pathophysiology of CNS diseases. For example, the neural stem cells obtained by the method of the invention can be used for screening for compounds that reverse, inhibit or prevent neurological diseases. In addition they can be used for screening for compounds that reverse, inhibit or prevent neural side effects of medicaments, for example diabetes medicaments. Preferably, said neural stem cells obtained by the method of the invention described herein are derived from diseased subjects.

In another aspect, the invention provides a therapeutic composition containing cells produced by any of the foregoing methods or containing any of the foregoing cell populations. Preferably, the therapeutic compositions further comprise a physiologically compatible solution including, for example, artificial cerebrospinal fluid or phosphate-buffered saline. Said therapeutic composition can be used to treat, prevent, or stabilize a neurological disease such as for example, Alzheimer's disease, Parkinson's disease, Huntington's disease, or ALS, lysosomal storage diseases, multiple sclerosis, or a spinal cord injury. For example, fibroblast cells, keratinocytes or adipocytes may be obtained by skin biopsy from the individual in need of treatment or from a healthy individual and reprogrammed to neural stem cells by the method of the invention. In one embodiment of the invention the neural stem cells are harvested and introduced into the individual to treat the condition. In another embodiment said neural stem cells are cultured under conditions suitable for differentiation into neurons, oligodendrocytes or astrocytes prior to introduction into the individual, and may be used to replace or assist the normal function of diseased, or damaged tissue. The great advantage of the present invention is that it provides an essentially limitless supply of patient specific human neural cells or compatible neural stem cells from healthy individuals with the same HLA type suitable for transplantation. The use of autologous and/or compatible cells in cell therapy offers a major advantage over the use of non-autologous cells, which are likely to be subject to immunological rejection. In contrast, autologous cells are unlikely to elicit significant immunological responses.

Another embodiment of the invention is the use of biobanks of neural stem cells for therapy of neurological diseases. The biobanks preferably comprise neural stem cells obtained from patients or healthy individuals with several HLA types. Transplanting cells obtained from a healthy donor to an individual in need of treatment with a compatible HLA type obviates the significant problem of rejection reactions normally associated with heterologous cell transplants. Conventionally, rejection is prevented or reduced by the administration of immunosuppressants or anti-rejection drugs such as cyclosporin. However, such drugs have significant adverse side-effects, e.g., immunosuppression, carcinogenic properties, kidney toxicity as well as being very expensive. The present invention should eliminate, or at least greatly reduce, the need for anti-rejection drugs, such as cyclosporine, imulan, FK-506, glucocorticoids, and rapamycin, and derivatives thereof.

With respect to the therapeutic methods of the invention, it is not intended that the administration of neural stem cells to a mammal be limited to a particular mode of administration, dosage, or frequency of dosing; the present invention contemplates all modes of administration, including intramuscular, intravenous, intraarticular, intralesional, subcutaneous, or any other route sufficient to provide a dose adequate to prevent or treat a disease. The neural stem cells may be administered to the mammal in a single dose or multiple doses. When multiple doses are administered, the doses may be separated from one another by, for example, one week, one month, one year, or ten years. One or more growth factors, hormones, interleukins, cytokines, small molecules or other cells may also be administered before, during, or after administration of the cells to further bias them towards a particular cell type.

SHORT DESCRIPTION OF THE FIGURES

FIG. 1: Schematic representation of the method for converting human fibroblast to irNSCs. Day 0: human fibroblasts were trypsinized and transfected in a small volume with a combination of genes and the nestin GFP reporter using the induction medium (N2B27 with FGF, EGF 30 ng/ml; BDNF 20 ng/ml; Fasudil 10 μM, Polybrene 4 μg/ml). Fibroblasts were plated in a normal tissue culture plate at a concentration of 10000-30000 cells/$cm^2$. Day 1: Media change with fresh induction medium. GFP/nestin positive (GFP+) irNSCs started to appear with very low frequency (~50 irNSC GFP+ out of 100000). Day 2: The GFP+ irNSCs were increasing in number and they started to move together forming cell clusters. Day 3: The cell clusters are organized in a clear spheroid structure that lifts off and starts floating as a GFP+ neurospheres. The neurospheres bigger than 20 μm were counted and harvested for further expansion.

FIG. 2: Schematic representation of the human nestin GFP reporter lentivirus. The fluorescent protein copGFP and the zeocin selectable marker were cloned under the expression control of a 1.8 kb enhancer fragment from the human nestin intron 2 linked to a minimal CMV promoter.

FIG. 3: irNSCs at day 1 of the reprogramming induction method. Upper panel: human untransformed fetal lung fibroblasts IMR90 (phase contrast). Lower panel: generation of irNSC GFP+ cells (phase contrast and GFP channel).

FIG. 4: irNSCs at day 2 of the reprogramming induction method. The cells tend to migrate close together and start to form a spheroid structure with a core of irNSCs GFP+ (phase contrast and GFP channel).

FIG. 5: irNSCs at day 3 of the reprogramming induction method. The spheroid structures formed at day 2 are now completely mature appear as neurospheres floating in the medium. The neurospheres have a dimension that ranges from 20-100 μm in diameter with a high density of cells. The irNSCs are labeled by the nestin GFP expression and can be indentified in almost all the neurospheres, although not all the neurospheres have the same proportion of irNSC GFP+ (phase contrast and GFP channel).

FIG. 6: Number of neurospheres generated with different combinations of genes.

FIG. 7: Attached neurospheres after transduction with Sox2-Bmi1. The attached neurospheres show a characteristic morphology of elongated bipolar cells. Lower panel: higher magnification of the irNSC GFP+ neuropsheres.

FIG. 8: Differentiated cells after 1 week EGF and FGF withdrawal. The irNSCs upon withdrawal of the proliferative growth factors give rise to cells with very thin protrusions stained positive for the neuronal marker tuj1.

FIG. 9: Generation of a batch of irNSC neurospheres for expansion and characterization. 3.6 million human fibroblasts IMR90 were trypsinized and infected in a small volume with: Sox2, Bmi1, nestin GFP reporter using the induction medium (N2B27 with FGF, EGF 30 ng/ml BDNF 20 ng/ml) supplemented with Fasudil 10 μM and Polybrene 4 μg/ml. From Day 4 to Day 8: The GFP+ neurospheres bigger than 50 μm were harvested and further used for expansion. Half of the neurospheres have been expanded using the expansion medium (N2B27 with FGF, EGF 30 ng/ml BDNF 20 ng/ml) with Fasudil and the other half without Fasudil. Day 15: Neurospheres grown in the expansion medium with Fasudil have a better morphology and clear and sharp borders (a hallmark of well-formed neurospheres, panel B); without Fasudil the neurospheres have bleary borders (panel A).

FIG. 10: Immunocytochemistry characterization of irNSC neurospheres for the expression of the NSCs markers Sox2 and Nestin. Day 15 irNSC neurospheres expanded with Fasudil have been plated on PO/Lam coated plates and after 48 h stained for Sox2 and Nestin expression. The irNSC neurospheres attached and irNSCs spread from the spheres. The irNSCs have a typical NSC morphology and were Sox2 and Nestin positive. Panel A: Merge and single channels DAPI, Sox2, Nestin; 20× magnification; Panel B: Merge channels DAPI, Sox2, Nestin; 10× magnification.

FIG. 11: Comparison of Fasudil versus Balanol-like-324 compound stimulation to generate irNSC neurospheres. Human fibroblasts IMR90 were trypsinized and infected in a small volume with: Sox2, Bmi1, nestin GFP reporter using the induction medium (NeuroCult® NS-A Proliferation Kit (Human, StemCells Technologies) with FGF, EGF BDNF 20 ng/ml; Heparin 2 μg/ml; Polybrene 4 μg/ml) supplemented with Fasudil 10 μM (hatched graph) or Balanol-like-324 compound 2 μM (black graph). Fibroblasts were plated in a normal tissue culture plate at a concentration of 10000-30000 cells/cm$^2$. Day 1: Media change with fresh induction medium. Day 4: The GFP+ neurospheres bigger than 50 μm were counted. The Balanol-like-324 small compound increased the efficiency of the neurospheres generation approximately twofold (1.9) and has a better reproducibility (STDEV, n=3).

FIG. 12: Pre-treatment of human fibroblasts with Valproic Acid (VPA) improves the yield of GFP+ irNSC neurospheres. Human fibroblasts IMR90 were pre-treated for 48 hours with or without the HDAC inhibitor Valproic Acid (2-propyl-pentanoic acid, monosodium salt) (1 mM) prior infection with: Sox2, Bmi1, nestin GFP reporter. Induction medium (NeuroCult® NS-A Proliferation Kit (Human, StemCells Technologies) with FGF, EGF BDNF 20 ng/ml; Heparin 2 μg/ml; Balanol-like-324 2 μM). Day 7: The Neurospheres bigger than 50 μm were counted (Panel A) and the average number of GFP+ irNSC per neurosphere is reported (Panel B). Representative pictures for the irNSCs neuropheres generated with the VPA pre-treatment (Panel C). The VPA pre-treatment did not significantly affect the number of neurospheres at day 7; although the VPA treatment increased (2.1 fold) the number of GFP+ irNSCs (STDEV, n=3).

FIG. 13: Defining a minimal pool of genes in combination with Sox2 and Bmi1 for efficient induction of irNSCs neurospheres. Human fibroblasts IMR90 were pre-treated for 48 hours with VPA (1 mM) prior infection with: Sox2, Bmi1, nestin GFP reporter plus different candidate genes to address their synergism. Induction medium: NeuroCult® NS-A Proliferation Kit (Human, StemCells Technologies) with FGF, EGF BDNF 20 ng/ml; Heparin 2 μg/ml and Balanol-like-324 compound 2 μM. Quantification at Day 7 of irNSCs neurospheres bigger than 50 μm. Mash1, Emx2, Foxg1, Pax6 and Sox11 synergize with Bmi1 and Sox2 to generate irNSC neuropheres.

FIG. 14: Generation of irNSC neurospheres from adult human dermal fibroblasts (HDFa). The adult human dermal fibroblasts are provided by the GIBCO (Cat. Number: C-013-5C). The adult human dermal fibroblasts were trypsinized and infected in a small volume with: Sox2, Bmi1, nestin GFP reporter using the induction medium (NeuroCult® NS-A Proliferation Kit (Human, StemCells Technologies) with FGF, EGF BDNF 20 ng/ml; Heparin 2 μg/ml) supplemented with Fasudil 10 μM. Day 8: irNSCs neurospheres are detected (representative pictures 2.5 and 10× magnification).

FIG. 15: Expansion of irNSC neurospheres using a combination of Ascorbic Acid, Sonic Hedgehog (Shh), Jagged1, DLL4 and FGF8 to obtain a monolayer culture of irNSCs GFP+. Human fibroblasts IMR90 were infected with: Sox2, Bmi1, Mash1 and nestin GFP reporter using the induction medium (NeuroCult® NS-A Proliferation Kit (Human, StemCells Technologies) with FGF, EGF BDNF 20 ng/ml; Heparin 2 μg/ml; Balanol-like-324 2 μM). Day 7: The neurospheres bigger than 50 μm were harvested and further expanded with the expansion medium (NeuroCult® NS-A Proliferation Kit (Human, StemCells Technologies) with FGF, EGF BDNF 20 ng/ml; Heparin 2 μg/ml; Balanol-like-324 2 μM; Ascorbic Acid 0.2 mM, SHH (Recombinant Human Sonic Hedgehog, Catalog Number: 1845SH) 500 ng/ml, FGF8 (Recombinant Human FGF8a Isoform, Catalog Number: 4745F8) 100 ng/ml, DLL4 (Recombinant Human DLL4, Catalog Number: 1506D4) 500 ng/ml, Jagged1 (Recombinant Human Jagged 1 Fc Chimera, Catalog Number: 1277JG) 500 ng/ml, conditioned media 1/10 from the hESC-derived NSCs cultured for two days in NeuroCult® NS-A Proliferation Kit (Human, StemCells Technologies) with FGF, EGF BDNF 20 ng/ml; Heparin 2 μg/ml. Representative pictures for the irNSCs neuropheres at day 14 expanded with expansion medium reported above (Panel A). The neuropheres have defined borders and it is possible to observe the protrusion of spines from the neurospheres (Panel B, zoom-in). At day 21 the expanded irNSC neurospheres were dissociated and plated on PO/Lam coated plates to obtain a homogenous monolayer culture of irNSCs GFP+ (Panel C, phase contrast and GFP channel of the irNSCs monolayer after 4 days in culture on the monolayer).

FIG. 16: Immunocytochemistry characterization of irNSC neurospheres for the expression of the NSC markers Nestin and the early neuronal marker Tuj1. Day 21 irNSC neurospheres generated as described in FIG. 15 were dissociated and plated in NSC self-renewal conditions (NeuroCult® NS-A Proliferation Kit (Human, StemCells Technologies) with FGF, EGF BDNF 20 ng/ml; Heparin 2 μg/ml) to test the expression of the Nestin marker (Panel A after 48 h, all the cells are Nestin+ and Tuj1−) or plated in differentiation conditions (NeuroCult® NS-A differentiation Kit (Human, StemCells Technologies) with BDNF 20 ng/ml) and stained for Tuj1 and Nestin at day 7 (Panel B, all the cells are Tuj1+ and few cells are Nestin+).

EXAMPLES

The method can be illustrated by reference to FIG. 1 herein, which depicts a method according to the invention being used for converting human fibroblasts to neural stem cells (NSCs). In this method human fibroblast were trypsinized at day 0, counted and their viability determined. Between $1.0\times10^5$-$3.0\times10^5$ trypsinized fibroblasts were then resuspended in the induction medium and the combination of genes delivered as lentiviruses. At the induction medium polybrene (hexadimethrine bromide) was added to increase the efficiency of the lentiviruses transduction. The infection was performed for 15 minutes in an eppendorf tube. In combination with the genes, a human Nestin GFP reporter was used. Nestin is a well known marker expressed specifically in NSCs. In the nestin reporter the fluorescent protein GFP is under expression of the human nestin promoter (FIG. 2), therefore it allows an easy screen for induced reprogrammed neural stem cells (irNSCs) GFP+.

The infected cells were plated in tissue culture plates using a concentration of 10000-30000 cells/cm$^2$ in the appropriate volume of induction medium. At day 1 the total induction medium was renewed. It was possible to identify some irNSC GFP+ (FIG. 3) with a clear change in morphology compared to the human fibroblasts. The irNSCs GFP+ acquired a bipolar and elongated morphology with a more condensed cytoplasm, typical of NSCs. Moreover, the irNSCs are growing in a packed monolayer culture that resembles the typical cell-to-cell interaction acquired in traditional NSC cultures for activating the pro-proliferative signal of the Notch pathway. At day 2 the irNSCs GFP+ were in a more mature state and started to form very packed clusters of cells. These clusters of irNSCs started to form a spheroid structure with a dense core containing irNSCs GFP+ (FIG. 4). At day 3 the spheroid structures were completely formed and started to lift off from the tissue culture plate floating as neurospheres in the medium. The neurospheres have a dimension of approximately 20-100 μm with clear borders and a core with a high density of cells, where it is possible to identify irNSCs GFP+ (FIG. 5).

To achieve the inventive breakthrough, it was necessary to use a specific combination of genes. The following list of genes involved in the maintenance of the NSC property in vivo and in vitro were retrieved from literature knowledge: Sox2 (Sox transcription factor and important marker for NSC), Brn2 (POU domain protein known to bind to Sox proteins. Reported binding of Sox2 and Brn2 on the nestin promoter. Brn2 KO mice have impairment of CNS development), Bmi1 (Protein involved in the regulation of the cell cycle, reported to increase expression of the p21 and p27 inhibitors of the cyclinE/cdk2 complex. CyclinE/cdk2 inhibition determines the lost of the retinoblastoma protein control on the cell cycle that results in a fast cell cycle during the self-renewal state of NSCs), Mash1 (described to be an important regulator for the proliferation of neural precursors in vivo), Sox11 (Sox protein reported to be expressed in SGZ in vivo), NCam (NSC marker in Flow Cytometry and expressed in different regions of the CNS), Kpna1 (better known as importin alpha5 responsible together with importin beta for the protein nuclear import in ectoderm derived tissues).

All genes were cloned as cDNAs into lentiviruses plasmids, and subsequently packaged into lentiviruses. The lentiviruses packaged particles for Sox2, Bmi1, Mash1, Sox11, NCam, Kpna1, nestin GFP reporter were transduced directly into human fibroblasts. Different combinations of genes were tested in the method described above. At day 3 it was possible to evaluate the success of the production of the irNSCs by counting the neurospheres generated. Only neurospheres bigger than 50 μm were taken into account.

As represented in FIG. 6 the transduction of the nestin reporter lentivirus without addition of Fasudil to the induction medium did not reprogram the human fibroblasts to irNSCs. With the addition of Fasudil to the induction medium the generation of neurospheres (around 50 μm) and some smaller (around 20 μm, not counted) were reported.

Neurospheres generated with our innovative method using the genes combination: Sox2-Bmi1 were harvested at day 3 and expanded for further 14 days. Expansion of the irNSCs neurospheres was a critical step. The neurospheres were cultured using the N2B27 medium supplemented with FGF, EGF, BDNF in special ultra-low non adherent plates (Corning). In order to achieve a homogenous population of irNSCs GFP+ neurospheres a cleaning procedure every 2-3 days was applied. During 14 days of expansion some neurospheres with low density of irNSCs GFP+ were not able to proliferate properly, most probably due to a contamination by not converted fibroblasts. Such kind of contaminated neurospheres were fallen apart in single cells that needed to be removed. At day 14, the neurospheres were tested for: attachment on poly-ornithine/laminin coated plates and generation of neuronal-like cells. For the attachment, 20-40 neurospheres/cm$^2$ were plated on poly-ornithine/laminin coated plates in the expansion medium supplemented just for the first day with Fasudil 10 μM, in order to improve cell attachment and spreading. At day 1 of culture was possible to show the attachment and spreading of the neurospheres (FIG. 7). At the centre of the spreading neurospheres we identified irNSCs GFP+ with a typical NSC morphology. The neurospheres were grown for additional three days and then just BDNF was added to the N2B27 (neuronal differentiating conditions). Upon EGF and FGF withdrawal the irNSCs changed morphology. They became more elongated and started to form neurite-like cellular protrusions. At day 7 of the differentiating conditions cells were fixed and stained for the neuronal marker tuj1 (FIG. 8).

Neurospheres expanded with Fasudil have a better morphology and clear and sharp borders (a hallmark of well-formed neurospheres, FIG. 9, panel B); without Fasudil the neurospheres have bleary borders (FIG. 9, panel A). The irNSCs have a typical NSC morphology and were Sox2 and Nestin positive (FIG. 10).

FIG. 11 shows that Rock kinase inhibitor Balanol-like-324 compound increases the yield of GFP+ neurospheres.

These evidences show that the method was able to convert human fibroblasts to irNSCs based on linked steps of genes transduction (best combinations: Sox2-Bmi1, Sox2-Bmi1-Mash1, Sox2-Bmi1-Sox11, Sox2-Bmi1-Emx2, Sox2-Bmi1-Foxg1 and Sox2-Bmi1-Pax6, see also FIG. 13) and chemically defined medium induction.

To increase the yield of irNSCs, human fibroblasts were pretreated with or without the HDAC inhibitor Valproic Acid (VPA, 2-propyl-pentanoic acid, monosodium salt). Towards this end, the human fibroblasts were incubated in DMEM/F12 supplemented with FBS 10% and L-glutamine supplemented with 1 mM VPA prior to infection (FIG. 12).

Materials and Methods

Figure 1:
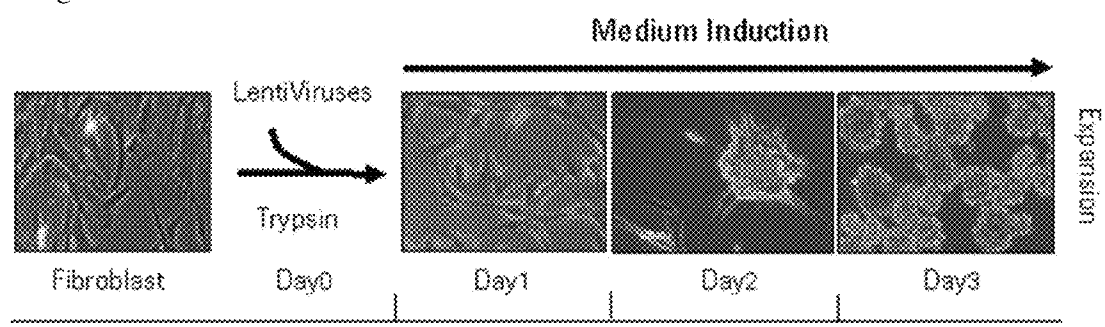
Figure 2:
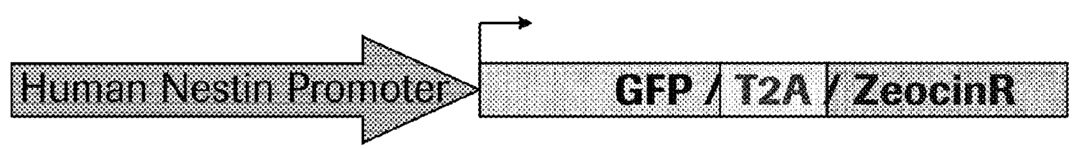
Figure 3:
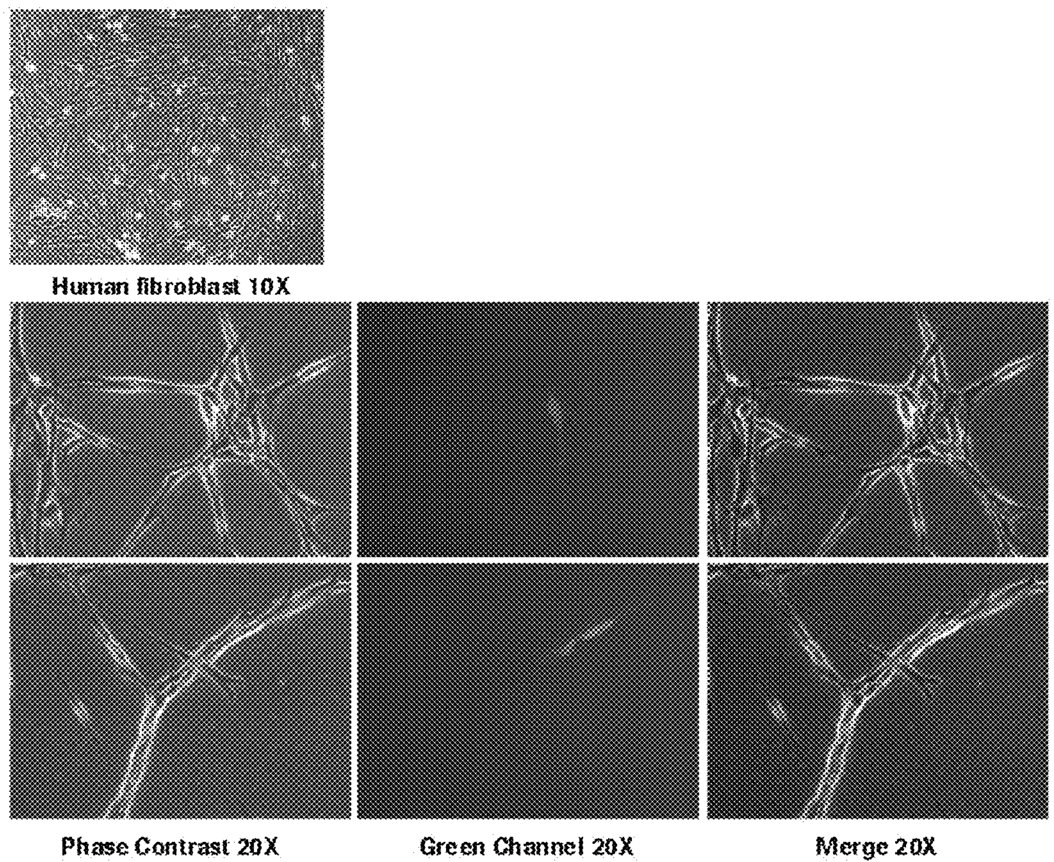
Figure 4:
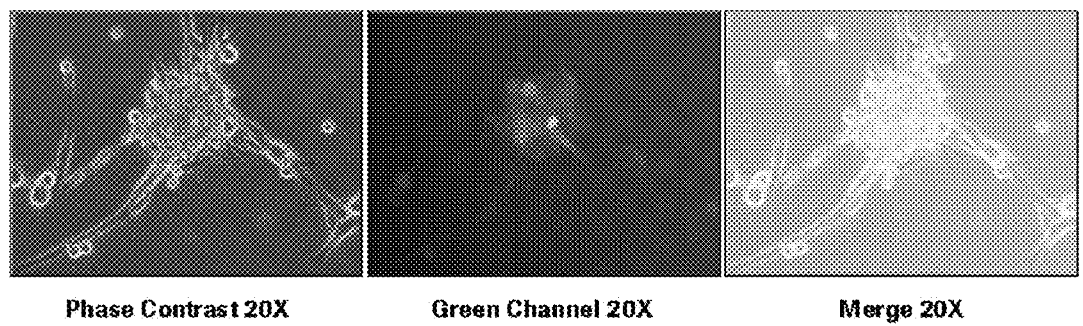
Figure 5:
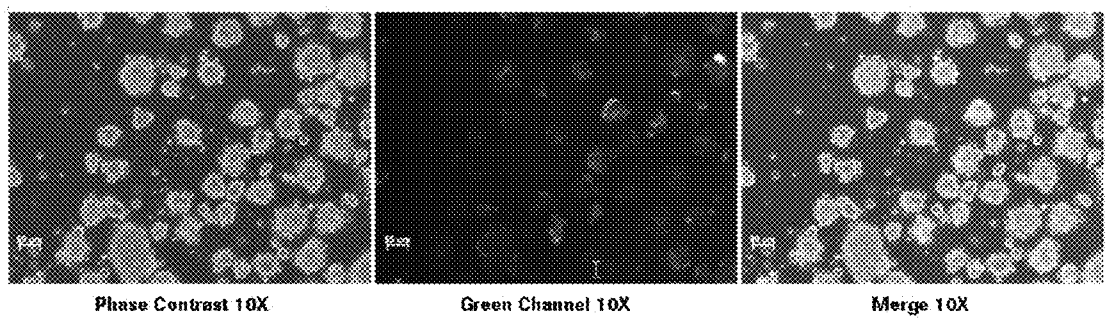
Figure 6:
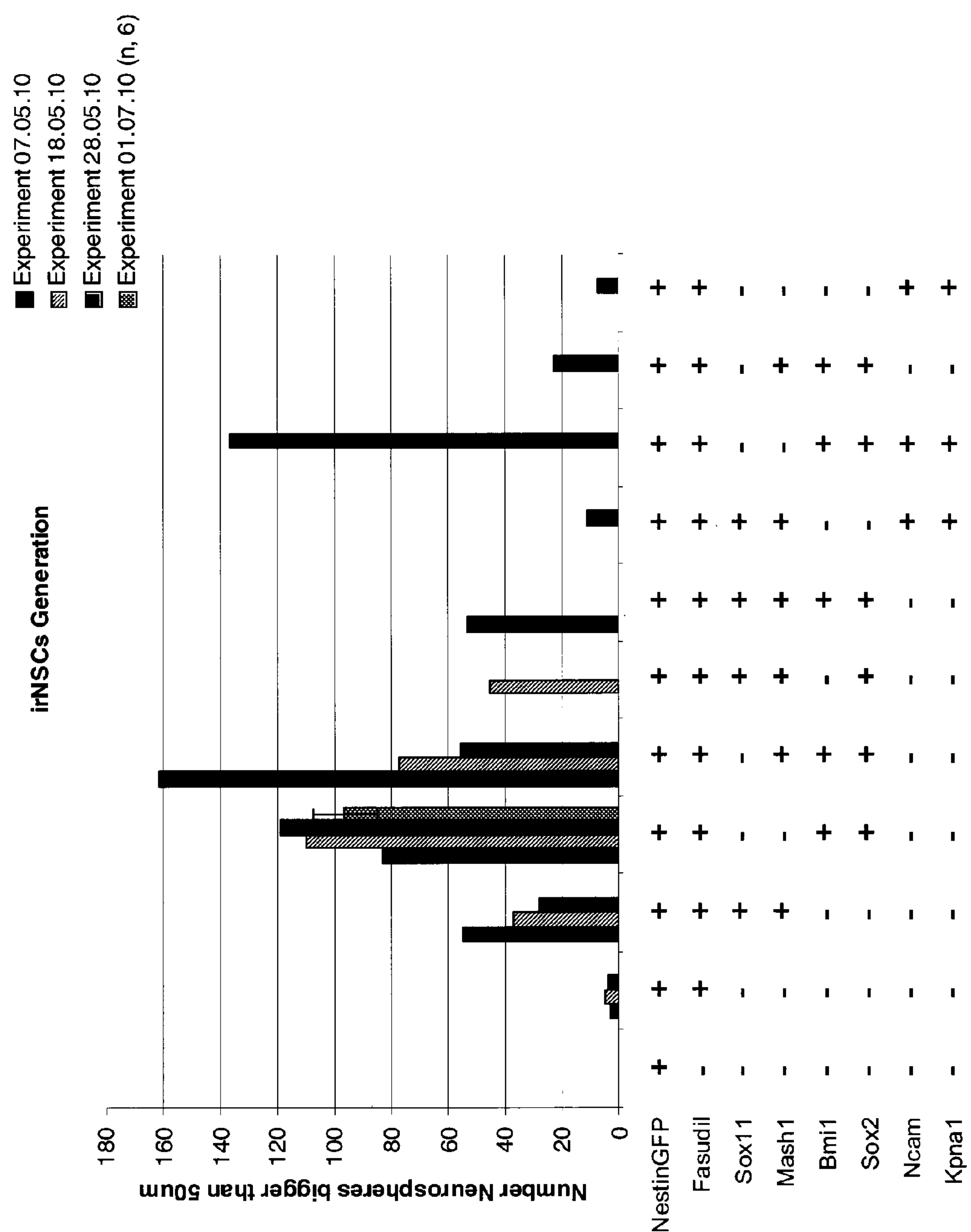
Figure 7:
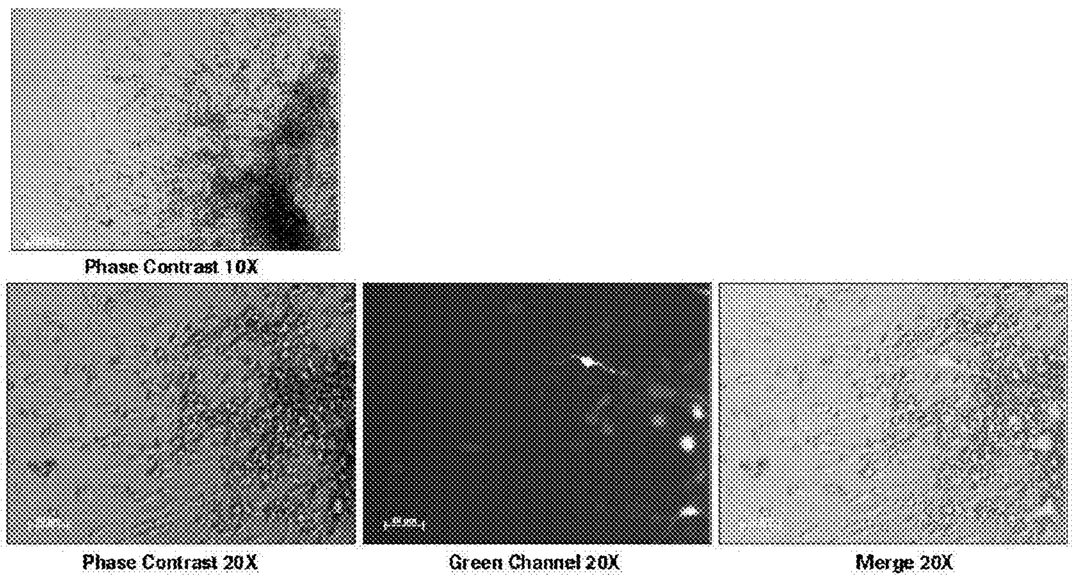
Figure 8:
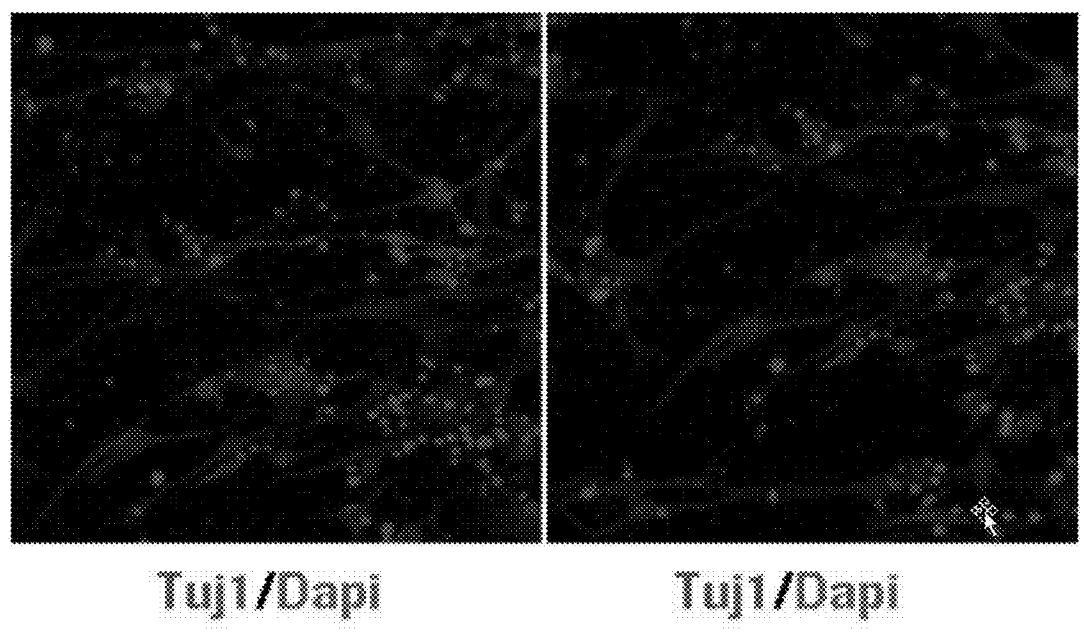
Figure 9:
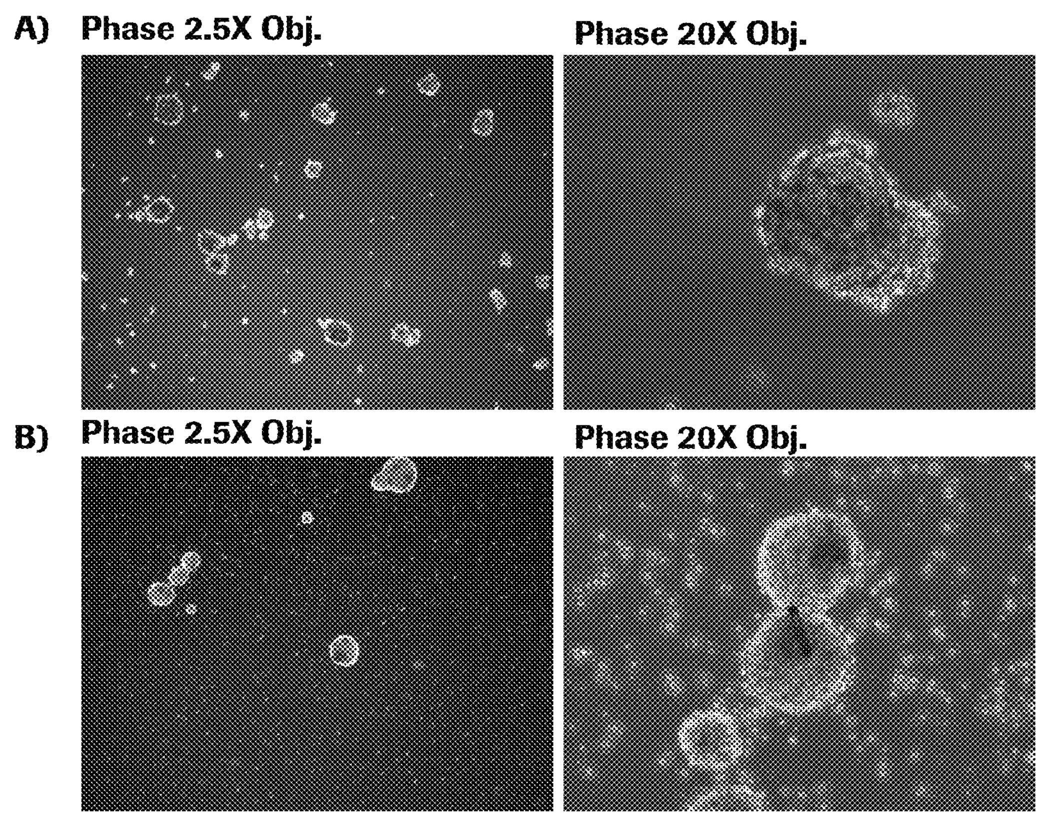
Figure 10:
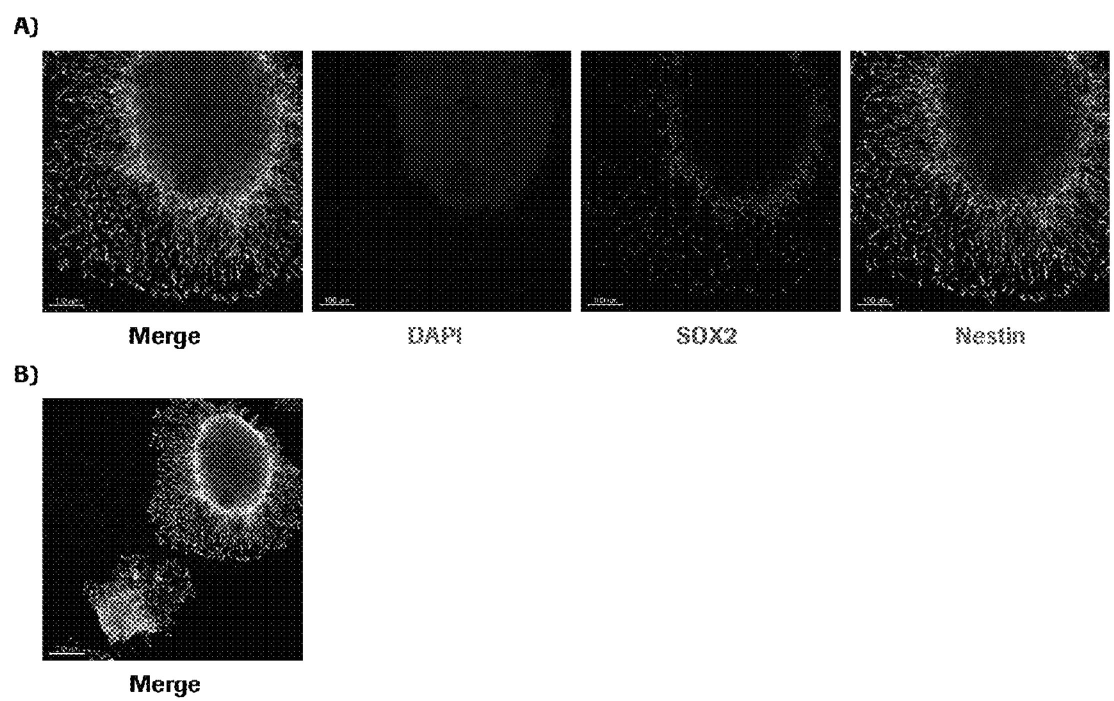
Figure 11:
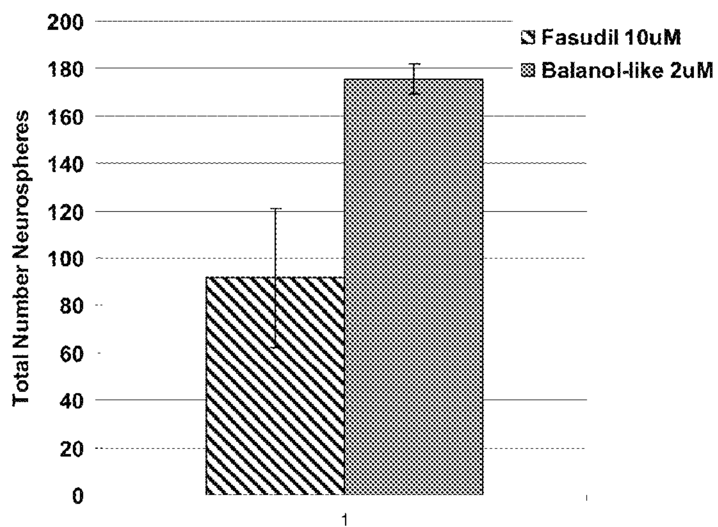
Figure 12:
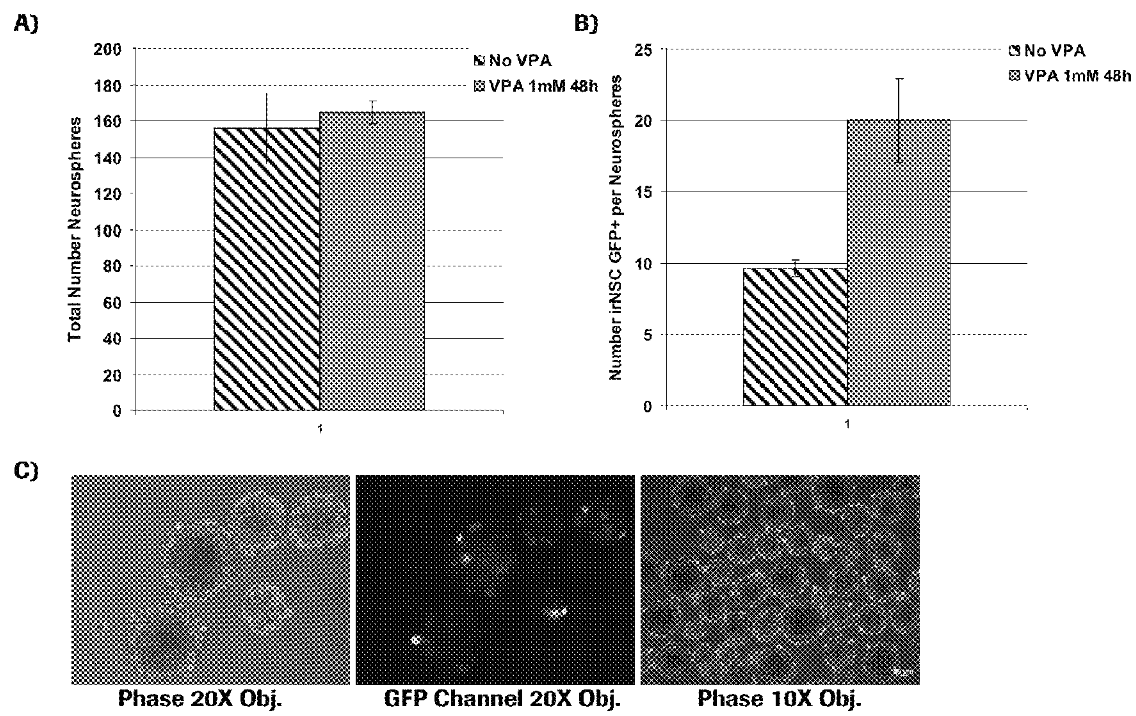
Figure 13:
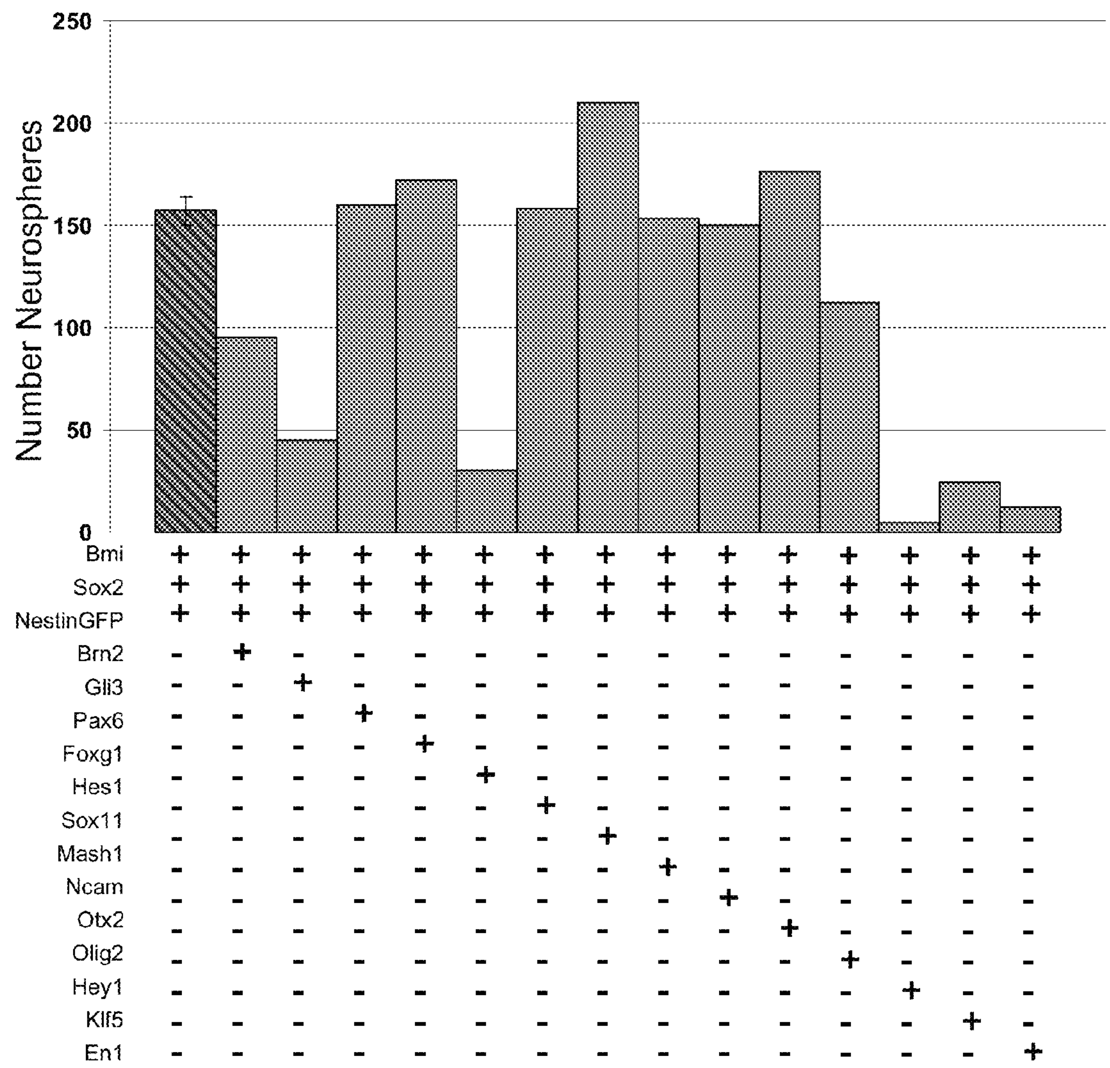
Figure 14:
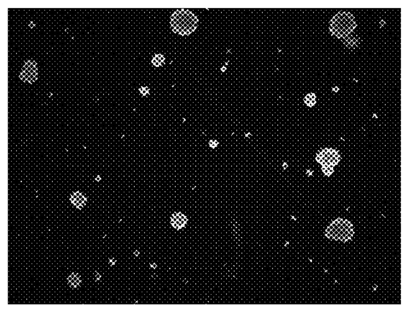
FIG. 14 shows the generation of irNSC Neurospheres from adult human dermal fibroblasts (HDFa).
Figure 14:
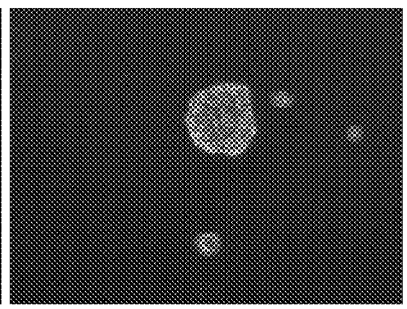
Figure 15:
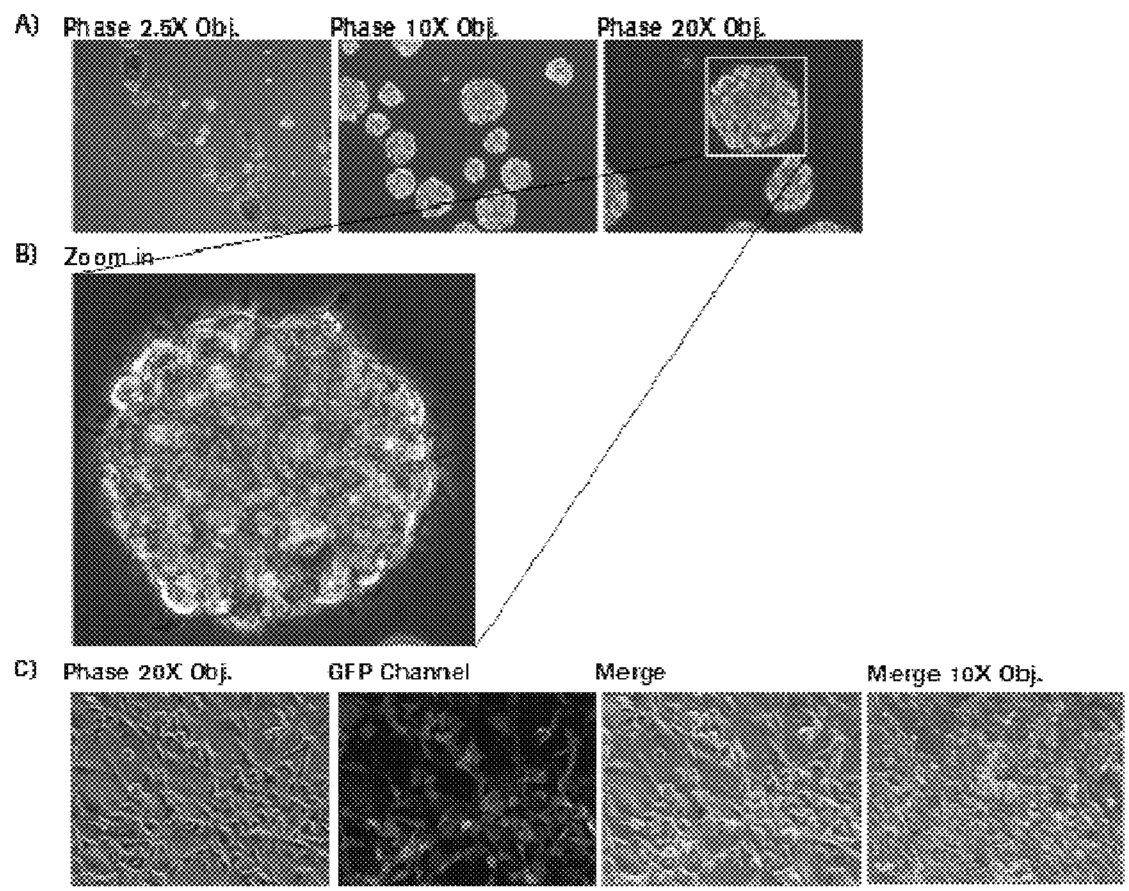
FIG. 15 shows the expansion irNSC Neurospheres using a combination of Ascorbic Acid, Sonic Hedgehog (Shh), Jagged1, DLL4 and FGF8.
Figure 16:
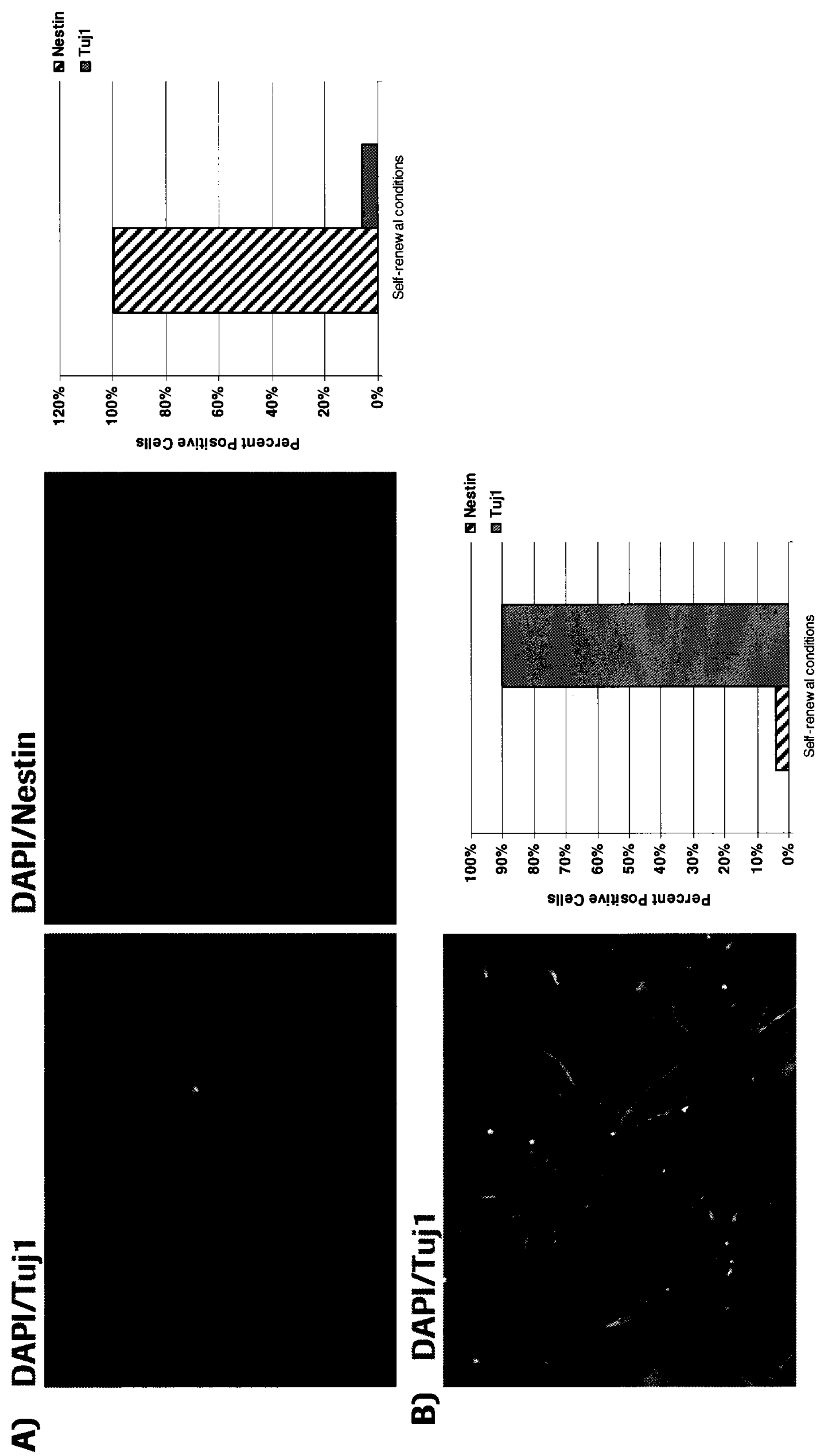
FIG. 16 shows Immunocytochemistry characterization of irNSC Neurospheres for the expression of the NSCs markers Nestin and the early neuronal marker Tuj1.

Cell Culture:

Induction Medium: N2B27 (N2B27 is a 1:1 mixture of DMEM/F12 (Gibco, Paisley, UK) supplemented with N2 and B27 (both from Gibco) supplemented with human EGF (Peprotech) 30 ng/ml, human FGF2 30 ng/ml (Peprotech), human BDNF (Roche) 20 ng/ml and Fasudil (Calbiochem) 10 μM or Balanol-like-324 compound (N-{(3R,4R)-4-[4-(2-Fluoro-6-hydroxy-3-methoxy-benzoyl)-benzoylamino]-azepan-3-yl}-4-hydroxy- 3,5-dimethyl-benzamide) 2 μM.

Expansion Medium: N2B27 supplemented with human EGF (Peprotech) 30 ng/ml, human FGF2 30 ng/ml (Peprotech), human BDNF (Roche) 20 ng/ml, or NeuroCult® NS-A Proliferation Kit (Human, StemCells Technologies) with FGF, EGF BDNF 20 ng/ml; Heparin 2 μg/ml; Balanol-like-324 2 μM; Ascorbic Acid 0.2 mM, SHH (Recombinant Human Sonic Hedgehog, Catalog Number: 1845SH) 500 ng/ml, FGF8 (Recombinant Human FGF8a Isoform, Catalog Number: 4745F8) 100 ng/ml, DLL4 (Recombinant Human DLL4, Catalog Number: 1506D4) 500 ng/ml, Jagged1 (Recombinant Human Jagged 1 Fc Chimera, Catalog Number: 1277JG) 500 ng/ml.

Differentiation Medium: N2B27 supplemented with human BDNF (Roche) 20 ng/ml, Laminin 2 μg/ml (Invitrogen).

Human fibroblasts: IMR90 foetal lung fibroblasts (ATCC Lot. Num. 580229699) or adult human dermal fibroblasts (GIBCO, Cat. Number: C-013-5C).

Lentiviruses: Prepackaged, ready-to use lentivirus particles were obtained from Sigma (Stemgent Reprogramming Lentivirus human Sox2, Catalog No. ST070012), Genecopeia (human Bmi1 Lentifect Lentiviral Particles, Catalog Nr. LP-B0015-Lv105; Sox11 Lentifect Lentiviral Particles, Catalog Nr. LP-MO425-LV105; Mash1 Lentifect Lentiviral Particles, Catalog Nr. LP-Z0740-LV105; human. Kpna1Lentifect Lentiviral Particles, Catalog Nr. LP-U1286-Lv105; NCam1 Lentifect Lentiviral Particles, Catalog Nr. LP-Z2645-Lv105) and SBI Systems Biosciences (Nestin GFP Reporter: pGreenZeo™-hNestin Transcriptional Reporter Virus, SR10035VA-1)

Titers Nestin GFP $1.45*10^5$/μl, BMI1 $4.3*10^5$/μl, Sox2 $1.07*10^4$/μl, Sox11 $3.2*10^6$/μl, Mash1 $4.7*10^6$/μl, NCam $3.3*10^4$/μl, Kpna1 $1.8*10^5$/μl.

Protocols:

1. Generation of the irNSCs:

200.000 IMR90 human fibroblasts infected with the lentiviruses for different genes combination (multiplicity of infection (M.O.I.) used for each single lentivirus 30) and the reporter nestin GFP lentivirus (M.O.I. used 10) in an eppendorf with 300 μl induction medium with polybrene (hexadimethrine bromide, Sigma) 4 μg/ml.

Incubate at room temperature for 15 min.

Plate the 300 μl in 1.7 ml induction medium in a well of a 6-well-plate tissue treated Day 1, renew the 2 ml of induction medium/each well Day 3, harvest of the neurospheres collecting carefully the 2 ml with the floating spheres Expand the neurospheres 2. Expansion of the Neurospheres:

Collect the medium with the floating neurospheres in 15 ml tubes from 3 wells of a 6-well-plate Let the spheres seed down for 10 min Remove the supernatant very carefully (single cells will not seed down and are aspirated with the supernatant).

Resuspend the spheres in 4 ml final volume expansion medium

Plate in a B6 plate ultra low adherent plate (Corning)

Incubate 2-3 days

Repeat the expansion procedure every 2-3 days till day 14 from the generation irNSCs 3. Differentiation Neurospheres:

Day 14 generation of the irNSCs and after the expansion procedure select under the stereo microscope round neurospheres with clear borders and rich in irNSCs GFP+

Plate 40 spheres in a well 24-well-plate previously coated with poly-ornhitine/laminin using the expansion medium with addiction of Fasudil 10 μM or Balanol-like-324 compound 2 μM.

The day after renew the expansion medium without Fasudil/Balanol-like-324 compound 2 μM.

Incubate for three days

Remove expansion medium and add differentiating medium

Renew differentiating medium after 3-4 days

Incubate for 3-4 days

Fix cells with PFA 4% and perform immunostainings

Protocol Staining irNSCs Neurospheres:

Neurospheres at day 15 were stained for characterization with the following antibodies: Mouse Nestin and Rabbit Sox2 O/N and then the secondary anti-mouse 488 and anti-rabbit 555 for one hour.

Primary antibodies:

Nestin Mouse, monoclonal, 1/500 dilution (MAB5326 Millipore)

Sox2 Rabbit, polyclonal, 1/500 dilution (AB5603MI Millipore)

Secondary antibodies:

Alexa fluor 488, IgG, 1/1 000 dilution, Goat anti mouse (A11029 Invitrogen)

Alexa fluor 555, IgG 1/1 000 dilution, Goat anti rabbit (A21429 Invitrogen)

What is claimed:

1. A method of producing Neural Stem Cells (NSCs), comprising:

a) providing human somatic cells selected from the group consisting of fibroblasts, adipocytes, or keratinocytes, b) reprogramming said cells to NSCs by introducing a first and a second gene, wherein the first gene is Sox2, and the second gene is selected from the group consisting of Bmi1, Mash 1, Sox11, Emx2, Foxg1 and Pax6; and c) culturing the cells of step (b) in medium comprising growth factors selected from the group consisting of FGF2, EGF and BDNF and a small molecule inhibitor of Rho-associated coiled-coil forming protein serine/threonine kinase (ROCK inhibitor), to produce NSCs.

2. The method of claim 1, further comprising d) incubating the NSCs under conditions suitable for proliferation of the NSCs.

3. The method of claim 1, wherein said cells of step a) are fibroblasts.

4. The method of claim 1, wherein the growth factors and small molecule of step c) are supplements of a chemically defined medium.

5. The method of claim 4, wherein the chemically defined medium is a serum free medium supplemented with insulin, transferrin and progesterone.

6. The method of claim 1, wherein the second gene of step b) is Bmi1.

7. The method of claim 6, wherein a third gene is introduced into the cells of step b) and the third gene is selected from the group of Mash1, Sox11, Emx2, Foxg1 and Pax6.

8. The method of claim 7, wherein the third gene of step b) is Mash1.

9. The method of claim 1, wherein the ROCK inhibitor is selected from the group consisting of 1-(5-Isoquinolinesulfonyl) homopiperazine, N-Benzyl-2-(pyrimidin-4-ylamino) thiazole-4-carboxamide, (+)-(R)-trans-4-(1-aminoethyl)-N-(4-pyridyl) cyclo-hexanecarboxamide dihydrochloride) and N-{(3R,4R)-4-[4-(2-Fluoro-6-hydroxy-3-methoxy-benzoyl)-benzoylamino]-azepan-3-yl}-4-hydroxy-3,5-dimethyl-benzamide.

10. The method of claim 1, wherein the somatic cells are pretreated with a histone deacetylase (HDAC) inhibitor.

11. The method of claim 1, wherein reprogramming of said somatic cells is achieved through delivery of a combination of at least two genes by a lentivirus.

12. A method of producing Neural Stem Cells (NSCs), comprising:

a) providing human somatic cells selected from fibroblasts, keratinocytes and adipocytes;

b) pretreating the human somatic cells with a histone deacetylase (HDAC) inhibitor;

c) reprogramming said human somatic cells to NSCs by introducing the genes Bmi1 and Sox2 and optionally at least one gene selected from the group consisting of Mash1, Sox11, Emx2, Foxg1 and Pax6, such introduction optionally effected by a lentivirus;

d) culturing the cells of step (c) in medium comprising at least one growth factor selected from the group consisting of FGF2, EGF and BDNF, and a small molecule ROCK inhibitor selected from the group consisting of 1-(5-Isoquinolinesulfonyl) homopiperazine, N-Benzyl-2-(pyrimidin-4-ylamino)thiazole-4-carboxamide, (+)-(R)-trans-4-(1-aminoethyl)-N-(4-pyridyl) cyclo-hexanecarboxamide dihydrochloride) and N-{(3R,4R)-4-[4-(2-Fluoro-6-hydroxy-3-methoxy-benzoyl)-benzoylamino]-azepan-3-yl}-4-hydroxy-3,5-dimethyl-benzamide to produce NSCs; and e) incubating the product of steps c) and d) under conditions suitable for proliferation of the NSCs.

* * * * *